United States Patent
Cohen

(10) Patent No.: US 11,899,009 B2
(45) Date of Patent: *Feb. 13, 2024

(54) RAPID REAL TIME MULTIPOINT PROCEDURE FOR OPTIMIZING SPERM STATE FOR USE IN ASSISTED REPRODUCTIVE TECHNOLOGIES

(71) Applicant: AREX LIFE SCIENCES, LLC, Watertown, MA (US)

(72) Inventor: Barb A. Cohen, Watertown, MA (US)

(73) Assignee: AREX LIFE SCIENCES, LLC, Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/691,004

(22) Filed: Nov. 21, 2019

(65) Prior Publication Data

US 2020/0116706 A1 Apr. 16, 2020

Related U.S. Application Data

(63) Continuation of application No. 14/777,407, filed as application No. PCT/US2014/023364 on Mar. 11, 2014, now Pat. No. 10,527,607.

(60) Provisional application No. 61/794,559, filed on Mar. 15, 2013.

(51) Int. Cl.
| | |
|---|---|
| *G01N 33/50* | (2006.01) |
| *G01N 33/569* | (2006.01) |
| *C12N 5/076* | (2010.01) |
| *A01N 1/02* | (2006.01) |

(52) U.S. Cl.
CPC ....... *G01N 33/5091* (2013.01); *A01N 1/0284* (2013.01); *C12N 5/061* (2013.01); *G01N 33/56966* (2013.01)

(58) Field of Classification Search
None
See application file for complete search history.

(56) References Cited

U.S. PATENT DOCUMENTS

| | | |
|---|---|---|
| 3,687,806 A | 8/1972 | Bovenkamp |
| 4,083,957 A | 4/1978 | Lang |
| 4,191,749 A | 3/1980 | Bryant |
| 5,021,244 A | 6/1991 | Spaulding |
| 5,514,537 A | 5/1996 | Chandler |
| 6,153,373 A | 11/2000 | Benjamin et al. |
| 6,489,092 B1 | 12/2002 | Benjamin et al. |
| 9,383,369 B2 | 7/2016 | Cohen |
| 2003/0068554 A1 | 4/2003 | Kitazawa |
| 2004/0053339 A1 | 3/2004 | Sutovsky |
| 2005/0114915 A1 | 5/2005 | Cohen |
| 2005/0192266 A1 | 9/2005 | D'Cruz et al. |
| 2011/0076667 A1 | 3/2011 | Cohen |
| 2012/0252000 A1 | 10/2012 | Cohen |

OTHER PUBLICATIONS

Definition of "peak"; Collins English dictionary. (1994). Glasgow: HarperCollins Publishers., accessed online on Feb. 11, 2022 at: https://www.collinsdictionary.com/us/dictionary/english/peak (Year: 1994).*
Baker, Sarah S., Monzy Thomas, and Catherine D. Thaler. "Sperm membrane dynamics assessed by changes in lectin fluorescence before and after capacitation." Journal of andrology 25.5 (2004): 744-751. (Year: 2004).*
Canadian Office Action for application serial No. CA 2,905,747, dated Jan. 2, 2020.
U.S. Appl. No. 14/777,407, filed Sep. 15, 2016, now U.S. Pat. No. 10,527,607.
Abeydeera et al. (1998), Birth of piglets preselected for gender following in vitro fertilization of in vitro matured pig oocytes by X and Y chromosome bearing spermatozoa sorted by high speed flow cytometry, Theriogenology 50: 981-988.
Aitken RJ and Baker MA (2008) The role of proteomics in understanding sperm cell biology. Int J Androl, 31, 295-302.
Alexenko et al. (2007), The Contrasting Effects of Ad Libitum and Restricted Feeding of a Diet Very High in Saturated Fats on Sex Ratio and Metabolic Hormones in Mice, Biol. Reprod. 77:599-604.
Austin, C.R., (1951), Observations on the Penetration of the Sperm into the Mammalian Egg, May 15, 1951, Aust. J. Sci. Res B, vol. 4, No. 4, 581-597.
Bailey JL (2010) Factors regulating sperm capacitation. Syst Biol Reprod Med, 56, 334-348.
BD Biosciences Webpage for Mouse Anti-Human CD46, Cat. #555948, accessed May 2019 at: http://www.bdviosences.com/eu/applications/research/t-cell-immunology/regulatory-t-cells/surface-markers/human/purified-mouse-anti-human-cd46-e43/p/555948 (year 2019).
Bedford JM (1970) Sperm capacitation and fertilization in mammals. Biol Reprod, Suppl-2, 128-158.
Blecher et al. (1999), A New Approach to Immunological Sexing of Sperm, Theriogenology 52: 1309-1321.
Brandriff et al. (1986), Sex Chromosome ratios determined by karyotypic analysis in albumin-isolated human sperm, Fertility and Sterility 46:678-685.

(Continued)

*Primary Examiner* — Robert J Yamasaki
(74) *Attorney, Agent, or Firm* — Bryan D. Zerhusen; Nicholas R. Herrel; CANTOR COLBURN LLP

(57) ABSTRACT

A method for adjusting the maturation state of mammalian sperm for use in assisted reproductive technologies (ART) is disclosed. A mammalian ejaculate is provided and incubated under controlled conditions. Aliquots of the ejaculate are assayed during incubation period at intervals to determine maturation state and changes in the maturation state by observing the percent positive cells in the aliquot. The assays are repeated with successive aliquots at intervals during incubation to observe real time changes in the maturation state. The ejaculate remaining is processed for the desired ART after the percentage of positive cells in the latest aliquot being assayed begins to decline.

14 Claims, 15 Drawing Sheets

(56) References Cited

OTHER PUBLICATIONS

Burns, B.M, et al. (2010) A review of factors that impact on the capacity of beef cattle females to conceive, maintain a pregnancy and wean a calf—Implications for reproductive efficiency in northern Australia, Animal Reproduction Science 122 (2010) 1-22.
Catalano et al. (2006), Exogenous shocks to the human sex ratio: the case of Sep. 11, 2001 in New York City, Human Reproduction 21: 3127-3131.
Chang M.C., (1958) Capacitation of rabbit spermatozoa in the uterus with special references to the reproductive phases of the female. Endocrinology, 63, 619-628.
Cohen-Dayag A., (1995) Sperm capacitation in humans is transient and correlates with chemotactic responsiveness to follicular factors. Proc. Natl. Acad. Sci. U.S.A., 92, 11039-11043.
Correa, J.R., (1997) Quantitative and Qualitative Characteristics of Frozen-Thawed Bovine Spermatozoa Recovered Via a Conventional and a Standardized Swim-Up Technique. Tohuku J. Exp. Med., 181, 267-274.
Cran and Johnson (1996), The predetermination of embryonic sex using flow cytometrically separated X and Y spermatozoa, Human Reproduction Update 2: 355-363.
Crews (1996), Temperature-Dependent Sex Dererrmination: The Interplay of Steroid Hormones and Temperature, Zoological Science 13: 1-13.
Downing, et al. (1991) Metabolic Toxicity of Flourescent Stains on Thawed Cryopreserved Bovine Sperm Cells, J. Histochem. and Cytochem. 39: 485-489.
Durand and Olive (1982), Cytotoxicity, Mutagenicity and DNA Damage by Hoechst 33342, J. Histochem. and Cytochem. 30:111-116.
Flesch, F., (2000) Dynamics of the mammalian sperm plasma membrane in the process of fertilization. Biochimica et Biophysica Acta, 1469: 197-235.
Foote R.H., (2002) Large batch freezing of bull semen: effect of time of freezing and fructose on fertility. J. Dairy Sci, 85, 453-456.
Fraser, L.R. (2010) The "switching on" of mammalian spermatozoa: molecular events involved in promotion and regulation of capacitation. Molecular Reproduction and Development 77(3):197-208.
Gadd, S.J., et al., "Binding of mouse monoclonal antibodies to human leukaemic cells vai the Fc receptor: a possible sourc of false positive reaction in spedificity screening," Clinical and Experimental Immumolgy, 54.3, 811, (1983).
Gadella B. (2013) Dynamic regulation of sperm interactions with the zona pellucida prior to and after fertilization. Reproduction, Fertility and Development, 2013, 25, 26-37 http://dx.doi.org/10.1071/RD12277.
Gianaroli, L., (2010) Birefringence characteristics in sperm heads allow for the selection of reacted spermatozoa for intracytoplasmic sperm injection. Fertility and Sterility, 93(3): 807-813 doi:10.1016/j.fertnstert.2008.10.024.
Harper, Claire V., et al., "Dynamic resolution of acrosomal exocytosis in human sperm", Journal of Cell Science, 121, 14, pp. 2130-2135, (2008).
Henkel, et al., "Sperm preparation for ART", Reproductive Biology and Endocrinology, vol. 1, Article No. 108, pp. 1-22 (2003).
Huszar et al., (2007) Fertility testing and ICSI sperm selection by hyaluronic acid binding: clinical and genetic aspects, Reproductive Biomedicine Online, May 2007;14(5):650-63.
International Preliminary Report on Patentability, dated Sep. 15, 2015, for PCT/US2014/023364.
International Search Report for PCT/US2014/023364, filed on Mar. 11, 2014, dated Aug. 14, 2014.
Jenkins T.G., (2011) The paternal epigenome and embryogenesis: poising mechanisms for development. Asian J. Androl., 13, 76-80.
Kim, K.- S., (2001) Differential Release of Guinea Pig Sperm Acrosomal Components During Exocytosis. Biology of Reproduction, 64: 148-156.
Lechniak (2003), Sperm Pre-Incubation Prior to Insemination Affects the Sex Ratio of Bovine Embryos Produced in vitro, Reprod. Dom. Anim. 38:224-227.
Mortimer D., (1991) Sperm preparation techniques and iatrogenic failures of in-vitro fertilization. Hum. Reprod., 6(2): 173-176.
Petrunkina, AM, et al., "Determinants of Sperm Quality and fertility in Domestic Species", Society for Reproduction, vol. 134, No. 1, Jul. 1, 2007, p. 1-17.
Shojaei H., (2012) Moribund sperm in frozen-thawed semen, and sperm motion end points post-thaw and post-swim-up, are related to fertility in Holstein AI bulls. Theriogenology, 77, 940-951.
Sills, et al., "H-X Antigen Expression Patterns in Human X—and Y. Chromosome-Bearing Spermatozoa", American Journal of Reproductive Immunology, vol. 40, pp. 43-47 (1998).
Supplementary European Search Report, dated Aug. 12, 2016, for EP 14768542.4; Publication No. EP2971058.
U.S. Appl. No. 14/777,407, filed Sep. 15, 2016, US 2016-0033483 A1.

\* cited by examiner

FIG. 23

Conventional

Collect Semen cool collection → Dilute at a standard time, regardless of sperm state, Cool to ~4C, aliquot doses and freeze → Run QC tests. release "QC pass" collections for sale

FERTAL Kinetic Assay

Collect Semen cool collection → Dilute by assay-detected fertile sperm state Cool to ~4C, aliquot doses, and freeze → Run QC tests, including FERTAL QC, release "QC pass" collections for sale

FIG. 24

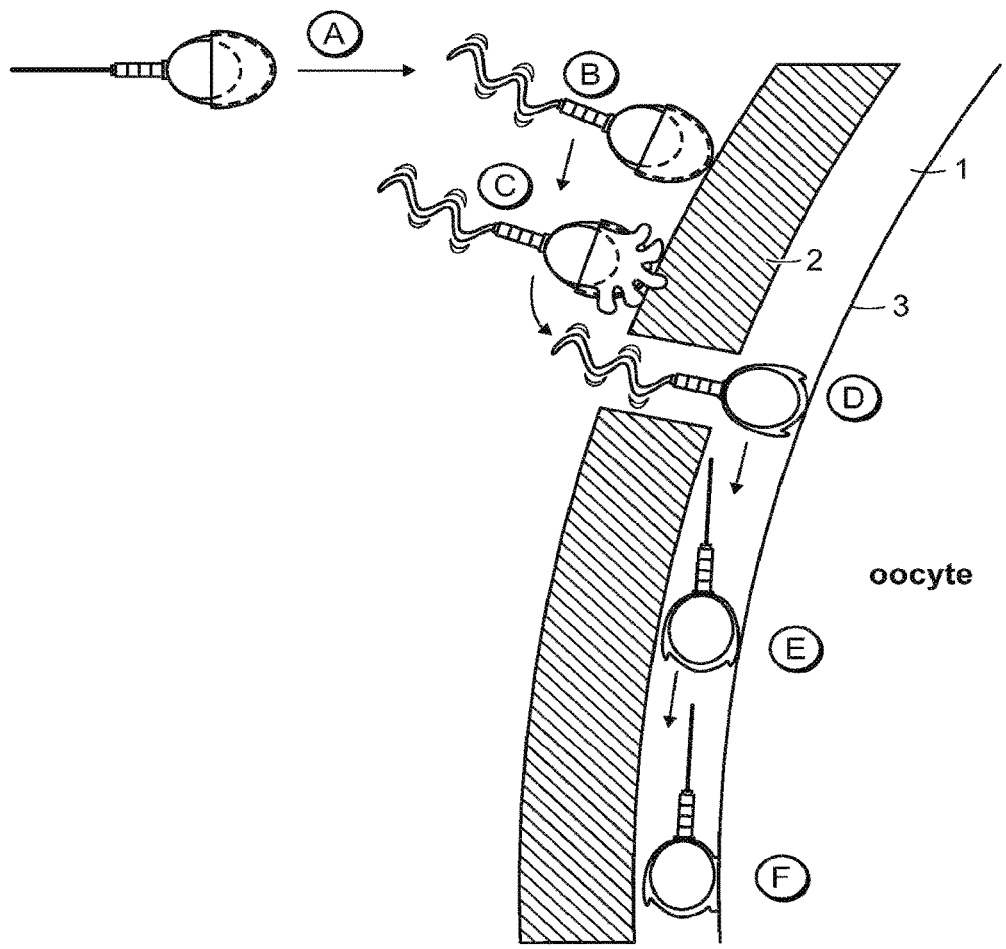

AM67 localization as detected by indirect immunofluorescence of guinea pig sperm undergoing acrosomal exocytosis. A) Indirect immunofluorescence assay was carried out and paired phase-contrast and fluorescence images of sperm were classified into four categories (sperm

RAPID REAL TIME MULTIPOINT PROCEDURE FOR OPTIMIZING SPERM STATE FOR USE IN ASSISTED REPRODUCTIVE TECHNOLOGIES

CROSS-REFERENCE TO RELATED APPLICATION

This application is a continuation application of U.S. patent application Ser. No. 14/777,407, filed on Sep. 15, 2015, which is a National Stage of International Patent Application Serial No. PCT/US2014/023364, filed Mar. 11, 2014, and published as International Patent Application Publication No. WO 2014/150480, which claims priority to and the benefit of U.S. Provisional Patent Application Ser. No. 61/794,559, filed Mar. 15, 2013, each of which are incorporated herein by reference in their entirety.

BACKGROUND

Treatment of mammalian semen to achieve a higher proportion of fertility and/or a higher proportion of sperm favoring one gender over another in assisted reproductive technologies such as, for example, artificial insemination can be advantageous. For example, a dairy herd would obtain economic and genetic herd quality benefit from an increase in numbers of cows pregnant at any given time and/or birthing a higher percentage of heifers relative to bulls. In such a situation, replacement animals for the herds are produced more efficiently. In addition, especially with low-beef value animals such as Holsteins, the expense of bull calves, and the potential cruelty these animals face when used in veal production is reduced.

The availability of replacement female animals born at the dairy farm eliminates the need to import replacements and the attendant risk of disease introduction into a herd. Additional advantages are found for businesses housing elite sires that produce dairy bull semen. Since these bulls are evaluated, i.e. "sire-proofed," for genetic quality through their daughters, an elite bull can be brought into semen production more quickly if he produces daughters more quickly and often. This speeds improvement of the sire genotype, with the attendant competitive advantage. Currently, many sires are also brought into production when they are even younger, because they are genotyped to prove their merit instead of waiting for large numbers of their daughters to be born. These very young sires produce small ejaculates with low sperm counts, making any fertility increase highly valuable because it generates more semen doses from these "thin" ejaculates. This further produces a savings in feed, veterinarian care, and other costs associated with bull farming. It also accelerates the improvement of the genetic base of dairy herds using semen from these processors, with the attendant economic savings to dairy farmer and semen processor alike.

In addition, achieving good fertility by increasing the quality of sperm used in artificial insemination is considered to be the single greatest determinant of the success or failure of dairy farms. Since "open" or non-pregnant cows do not lactate and are therefore not productive, they decrease profit. Consequently, any increase in fertility is considered worthwhile. Fertility is important for all types of animals raised for dairy or for meat such as goats, sheep, cattle, buffalo, camels, swine, etc.

In another example, increased sperm quality can lead to improvement and/or expansion of a particular population of animals. For instance, sperm collected from champion animals, such as cattle or other livestock and particular breeds of dogs and cats, is commonly used for artificial insemination to increase the probability of maintaining particular features in the gene pool. Sperm quality is particularly important in the breeding programs directed to exotic and endangered animals where the number of captive individuals is limited. Here, the ability to increase overall birth rates, thereby increasing the potential for rapid expansion of the population, is critical for success.

In another example, the personal suffering and costs associated with human infertility can in many cases be reduced through increasing sperm quality. Couples whose infertility is caused by low sperm count or poor sperm motility can benefit by increasing the number of viable sperm that result after the washing and preparation steps needed prior to intrauterine artificial insemination (IUI) or intracytoplasmic sperm injection (ICSI) or in vitro fertilization (IVF). Even couples with certain female-factor issues can overcome these issues by having access to more fertile sperm in higher numbers applied during insemination when healthy ejaculates are prepared in a way that increases sperm integrity.

With respect to gender bias, the suffering and costs of human sex-linked diseases can be reduced through birth of females in affected human families. Female births are the only way to eliminate over 300 X-linked diseases, many of which shorten and impair quality of life and create staggering medical costs. Currently, the costs and suffering associated with these diseases can be decreased through pre-implantation genetic diagnosis. In this process, eggs are harvested by laparoscopy following injections of hormones and fertility drugs. Eggs are fertilized in vitro and, after embryos have reached sufficient size, a single cell is microdissected from each embryo for genetic analysis. A suitable unaffected female embryo is chosen for implantation. Alternatively, sperm is collected and treated with mutagenic dye in preparation for fluorescent activated cell sorting (FACS). X-bearing sperm are obtained, however, they are so damaged that the sperm nucleus must be injected into an isolated egg in vitro using intracytoplasmic egg injection. Embryos are then cultured and implanted in recipients. Both of these techniques are expensive and raise unresolved questions about the effect of either hormonal treatments of the recipient or of-exposure to DNA-binding dyes and laser light, with respect to their cytotoxicity and mutagenic potential (Downey et al. (1991) J. Histochem. and Cytochem. 39: 485-489; Durand and Olive (1982) J. Histochem. and Cytochem. 30:111-116).

The scientific literature describes several methods for achieving gender bias through treatment of mammalian semen. They differ in process; some involve physical separation of sperm while others do not. They also differ at point of application; to sperm, to female mammals. What they share in common is that they cannot be applied effectively on-site.

Fertility issues with prior art technologies have typically restricted their use to virgin heifers, which are less stressed and therefore have higher fertility than cows that have experienced the stress of lactation.

For example, several methods have been reported for generating sex bias by physical separation of sperm, all of which involve complex laboratory manipulations and equipment. Fluorescence activated cell sorting (FACS) resolves sperm into X (female) and Y (male) bearing pools, after cell labeling with mutagenic DNA-binding dyes to reveal chromosome content (Abeydeera et al. (1998) Theriogenology 50: 981-988; Cran and Johnson (1996) Human Reproduction Update 2: 355-363). Methods of artificially biasing the sex of mammalian offspring through physical separation have also included methods based upon density sedimentation of spermatozoa (e.g. Brandriff et al. (1986) Fertil. Steril. 46:678-685) and by separating the population of spermatozoa into fractions that differ by the sex-linked electrical charge resident thereon (U.S. Pat. No. 4,083,957). Methods have also been described that rely on mechanical sorting of sperm by sex-type. U.S. Pat. No. 5,514,537, for example, uses a column packed with two sizes of beads. The large beads are of a diameter so that the smaller beads will fall between the interstices created between the larger beads. Then the interstices between the smaller beads allow Y-bearing sperm to enter them while the X-bearing sperm are excluded, thereby effecting separation of the two subpopulations. Separation based on immunological methods and cell surface markers have also been proposed (Blecher et al. (1999) Theriogenology 52: 1309-1321). In another example, U.S. Pat. No. 3,687,806 discloses an immunological method for controlling the sex of mammalian offspring using antibodies that react with either X-bearing sperm or Y-bearing sperm which uses an agglutination step to separate bound antibodies from unaffected antibodies. U.S. Pat. No. 4,191,749 discloses a method for increasing the percentage of mammalian offspring of either sex by using a male-specific antibody coupled to a solid-phase immunoadsorbant material to selectively bind male-determining sperm while female-determining sperm remain unbound in a supernatant. U.S. Pat. No. 5,021,244 discloses a method for sorting living cells based upon DNA content, particularly sperm populations to produce subpopulations enriched in X-bearing sperm or Y-bearing sperm by means of sex-associated membrane proteins and antibodies specific for such proteins.

Some methods have combined various aspects of the immunological and mechanical separations such as U.S. Pat. Nos. 6,153,373 and 6,489,092 which use antibodies coupled to a magnetic particle for separation of sperm.

Separation based on a miniscule size difference between X- and Y-bearing sperm has also been attempted (Van Munster et al. (1999) Theriogenology 52: 1281-1293; Van Munster (1999) Cytometry 35: 125-128; Van Munster 2002 Cytometry 47: 192-199).

In addition, sex bias without physical separation of sperm into X and Y bearing classes has been described. For example, stress (Catalano et al. (2006) Human Reproduction 21: 3127-3131), good or poor physical condition (Trivers and Willard (1973) Science 179:90-92), feed composition (Alexenko et al. (2007) Biol. Reprod. 77:599-604), temperature (Crews (1996) Zoological Science 13: 1-13) and other factors (Wedekind (2002) Animal Conservation 5:13-20) have been shown to affect offspring sex ratio.

Lechniak (2003, Reprod. Dom. Anim. 38:224-227); has also shown that time-based production of a sex bias in semen can occur when semen is held for various times before use in insemination for in vitro fertilization. However, the exact time course of activation of sperm from its dormant state at the time of collection, through its various metabolic states of fertility, until the sperm finally become infertile and atrophied, varies between different species of mammals, and also between different individuals of the same species, and even between ejaculates obtained from the same individual animal.

This large degree of variability in time course from semen samples collected from the same individual led those skilled in the art to conclude that a fertile semen sample having a gender bias could not be reliably obtained simply by processing a sample for insemination after a standard period of time after collection of the semen sample.

US Patent Publication 2011/0076667 discloses a method wherein a prior ejaculate from a source or type of mammal or specific source is processed under controlled conditions and a biomarker monitored at a plurality of times to determine a time profile of expression of a marker indicative of a desired trait for the desired sperm. Using that time profile, the maximum level of expression of the marker is determined. Then, a jump point is determined prior to that maximum level of expression, and the time difference between the jump point and the maximum level of expression is calculated. Subsequently, when obtaining further semen from that source or type of mammal, for real time processing of the semen, every ejaculate is incubated under the same controlled conditions and aliquots are monitored at a plurality of times to follow the expression of the marker until the level of expression at the pre-selected jump point (based on the reference sample) is reached. Then, the pre-determined time shift, i.e., the difference between the time of the maximum and the jump point (based on the prior ejaculate) is used to determine the desired time for processing the semen for use in artificial insemination. Although that process, which monitors every new ejaculate in real time for processing, can obtain substantially better results than other known prior art methods, it requires processing of a prior ejaculate to determine a time shift and still provides inconsistent results.

Therefore, there remains a need in the art to provide a procedure on which one can reliably depend to provide a semen sample containing sperm which have a desirable trait such as, for example, a fertile, gender biased semen sample. Ideally, the assay could be performed without the need for a specialized laboratory and highly trained professional.

Sperm become able to fertilize—capacitate—at wide-ranging times spanning hours that are unique to each ejaculate. Semen testing is not done at the same time as insemination or as freezing doses of sperm, meaning the status of the sperm at the time of insemination is not known. This is one reason semen tests do not correlate with fertility. A single-point assay of semen may indicate poor quality, when it may have simply been tested too early. Conversely, the semen may test well but be past its prime at insemination or freezing. This can occur because (1) single point assays do not identify the optimal state of sperm and (2) therefore, sperm cannot be stabilized in the optimal state.

One in six couples is affected by reproductive issues, including infertility. Many interventions exist for female-factor infertility, but male-factor infertility has few good options available. Sperm assays exist, but people are pessimistic about their utility. This is understandable as explained above, because the assays currently in use take a photograph of the sperm, i.e., a snapshot in time.

These assays are not applied to ejaculates in real time, that is immediately post-collection and at repeated time points, —to reveal the dynamic and changing nature of sperm. These changes include acquisition, at a time unique to each ejaculate—of abilities such as fertilizing ability, or of reaching the state of maximal fertility for that ejaculate, or of ability to successfully resist damage from processes such as freezing and vitrification, or of ability to produce gender bias, the gender bias being useful for example, in dairy cattle calvings. Only very fast real time assays can do this—run as multipoint assays starting immediately after ejaculation and repeated during the time period that mammalian sperm undergoes maturation prior to insemination. Fast assays applied this way (according to Applicant's novel methods and products described herein) enable optimization of sperm properties by customizing sperm handling to the unique timing of every ejaculate's sperm maturation. To accomplish such a goal, the present Applicant has concluded that a rapid multipoint real time assay is required.

Evaluating a semen sample according to the real time methods described herein enables optimizing the timing for processing a semen sample for assisted reproductive technologies according to the desired performance of the sample, for example, increased fertility.

SUMMARY OF THE INVENTION

Fertility of a single ejaculate changes from completely infertile at ejaculation to highly fertile and back to infertile, depending on the condition of the sperm in it. In natural mating, sperm mature and acquire fertility during their ascent of the female reproductive tract. Despite this, in vitro use of rapid, repeat monitoring that reports the changing sperm fertility state in an ejaculate has not been available. Applicant has tried to employ a time shift during the measurement to processing procedure that now has been found to be imprecise and, therefore, detrimental to consistent results. Hence, it has been impossible to correctly and consistently adjust the state of sperm in an ejaculate to the different states needed for the different types of Assisted Reproductive Technologies (ART). As a result, when using the previous process, sperm can be in a suboptimal fertility state when inseminated in ART, causing economic losses and medical burdens.

The presently presented rapid repeat monitoring assay detects changes in sperm—after ejaculation but before insemination—that indicate an ejaculate's sperm maturational state and enable stabilization of sperm in that state without the adverse effects of a lag time.

Thus, the present invention provides a method for adjusting the maturation state of mammalian sperm for use in assisted reproductive technologies (ART), said method comprising: providing a mammalian ejaculate; incubating the ejaculate under controlled conditions; assaying an aliquot of the ejaculate during incubation period to determine maturation state by observing the percent positive cells in the aliquot; repeating the assaying step with successive aliquots at intervals during incubation to observe real time changes in the maturation state; and processing the ejaculate remaining for the desired ART after the percentage of positive cells in the latest aliquot being assayed begins to decline.

Certain preferred embodiments of the invention include, for example, one or more of the following features:
the providing step includes collecting the mammalian ejaculate from a mammal using a collection device prewarmed to about the body temperature of the mammal;
the mammal is bovine and the collection device is prewarmed to a temperature in the range of about 30-40° C.;
the incubating step includes controlling the temperature of the ejaculate at a temperature in the range of about 4° C. to room temperature;
the mammal is bovine and the incubating step includes controlling the temperature of the ejaculate at a temperature in the range of about 14 to 15° C.;
the assaying step includes: mixing the aliquot with reagents capable of reacting with a marker indicative of sperm cell maturation, wherein the reaction produces fluorescence in connection with a positive reaction with a sperm cell; and determining a percentage of positive cells;
the reagents include an antibody or an antibody Fc region that interacts with the marker and the antibody is labeled with a fluorescent label;
the reagents include a primary and a secondary antibody that is labeled with a fluorescent label;
the reagents include a stabilizer for the sperm cells;
the determination of percent positive cells is made by a method selected from the group consisting of antibody-based, dye-based, motility-based and microscopy based procedures;
processing includes stabilizing the ejaculate remaining for further processing for the desired ART; and
further processing includes making straws having a predetermined amount of sperm cells and freezing the straws for artificial insemination.

In accord with the present invention, semen in the ejaculate is collected and maintained in a tightly controlled environment. A fast monitoring assay is run repeatedly post-ejaculation but before insemination, to monitor sperm state and permit adjustment of an ejaculate's sperm condition to the different states needed for different types of ART, such as insemination (e.g., vaginal insemination, insemination into the uterus (IUI)), in vitro fertilization (IVF) and intracytoplasmic sperm injection of the egg). Sperm then can be stabilized in the different required states and will thereby produce improved fertility.

Stabilization of the sperm different required states, as desired, in accord with the present invention can produce improved fertility and/or skew the gender ratio when used in ART. Thus, the profitability of agricultural operations can be increased. For example, on dairy farms, creating more female births gives the farmer more cows to milk, and more cows that produce milk because they have been pregnant. For intrauterine insemination (IUI) of cows with frozen sperm doses, sperm that have been adjusted by Assay to a more mature state perform better. They increase pregnancy rates or produce more female calves on dairy farms as compared to sperm from the same ejaculate that were not permitted to mature before freezing. Further, in the clinic, the suffering associated with human infertility may be reduced.

Using a rapid, multipoint real time monitoring procedure in accord with the present invention, the maturational status of sperm after ejaculation but before insemination can be adjusted. This can produce a surprising improvement in outcome. For example, an unexpected, commercially valuable 7% increase in cattle fertility can be obtained. This is important because it has been reported that dairy farmers earn on average only $75 per year per cow, and a 1% fertility increase provides an additional $20 per cow! Many have tried to improve fertility but the 1% increase is agriculture's 4 minute mile and greater increases are not currently considered possible.

The semen samples useful in the practice of the present invention are mammalian, preferably including, but not limited to human, bovine, ovine, caprine, equine, canine, feline and murine.

Marker(s), useful in the practice of certain preferred embodiments of the present invention, that are being assayed before insemination of an individual semen sample which is being adjusted for desired state of maturation according to the methods described herein, can be an Fc receptor. An Fc receptor as used herein encompasses a ligand that binds to a region other than the variable domain of an antibody. Accordingly, an Fc receptor as used herein encompasses a ligand that binds to the constant region of an antibody, for example to a constant domain of an antibody. In another embodiment the assay comprises more than one marker. Markers or biomarkers useful herein provide expression correlating to sperm maturation reflected as a measurement over time of an expression pattern of one or more biomarkers, against which maturation can be correlated.

Terminology Used in this Application

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies, and so forth. Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Unless otherwise stated, all ranges described herein are inclusive of the specific endpoints. The following terms are provided below.

As used herein, the term "semen sample" includes any semen sample collected from an ejaculate of any mammal, including, but preferably not limited to, human, cattle, goats, sheep, buffalo, swine, horses, cats, dogs, rat, mouse, rabbits, hamsters and endangered species of mammals. A semen sample can be obtained from both first and second ejaculates, and electro ejaculated collections, for example from bull studs.

As used herein, the term "maturation" is the process of developmental changes that sperm undergo after ejaculation, whether in vitro or in vivo. Maturational changes begin before sperm are capacitated and include the capacitation process as part of the later stages of maturation.

Capacitation is an imprecise term because definitions vary in the scientific literature. Some have broadly defined capacitation as the functional modifications that render sperm competent to fertilize an egg. Historically, more limited definitions restrict capacitation to the changes that occur in sperm within the female reproductive tract and/or to changes that occur at the later stages of sperm maturation. As used herein, the more restrictive definition of "capacitation" is used, i.e., changes that occur in vivo or in vitro in late maturity, in which sperm immediately become able to fertilize an egg.

As used herein, the term "fertility" with respect to sperm in a semen sample, refers to the ability of the sperm to fertilize an egg and create a viable embryo, fetus and live-born animal. This ability changes as the sperm age, and changes differentially with respect to whether the sperm is carrying an X chromosome or a Y chromosome.

As used herein, the term "room temperature" is meant to refer to an environment in which the assays of the invention are performed, typically in the range of about 20-25° C.

The term "marker" and "biomarker" may be used interchangeably and includes, but is not limited to, a ligand, a lectin, an enzyme and a receptor, which is expressed on the surface of the sperm, or internally, or both, and/or in the seminal fluid. In some embodiments, the marker is a morphological change in an acrosome which can be viewed, for instance, using bright field or phase contrast microscopy. With respect to acrosome morphology, over time the surface of the acrosome's membrane appears increasingly ruffled, with exosomes later being released. In some embodiments a marker can be cryptic at some stages of metabolism, and not detected.

As used herein, the term "antibody," includes, but is not limited to a polypeptide substantially encoded by an immunoglobulin gene or immunoglobulin genes, an IgG antibody, an IgM antibody, or a portion thereof, which specifically bind and recognize an analyte, antigen or antibody. An antibody or fragment thereof comprises an antibody or fragment thereof which is isolated from a natural source, for example an animal, mammal, mouse or human. Alternatively, an antibody or antibody fragment is produced using synthetic processes, including but not limited to recombinant methods, and chemical synthesis. "Antibody" also includes, but is not limited to, a polypeptide substantially encoded by an immunoglobulin gene or immunoglobulin genes, which specifically binds and recognizes the antigen-specific binding region (idiotype) of antibodies produced by a host in response to exposure to the analyte or immunogen.

As used herein, the term "antibody," encompasses polyclonal and monoclonal antibody preparations, as well as preparations including monoclonal antibodies, polyclonal antibodies, hybrid antibodies, altered antibodies, F(ab')$_2$ fragments, F(ab) fragments, F(c) fragments, F$_v$ fragments, single domain antibodies, chimeric antibodies, humanized antibodies, dual specific antibodies, bifunctional antibodies, single chain antibodies, and the like, and functional fragments and multimers thereof, which retain specificity for an analyte or antigen. For example, an antibody can include variable regions, or fragments of variable regions, and multimers thereof, which retain specificity for an analyte or antigen. See, e.g., Paul, Fundamental Immunology, 3rd Ed., 1993, Raven Press, New York, for antibody structure and terminology. Alternatively, the term "antibody" comprises a fragment thereof containing the constant region, in particular the Fc region. The antibody or portion thereof, may be derived from any mammalian species, e.g., from a mouse, goat, sheep, rat, human, rabbit, or cow antibody. An antibody or fragments thereof, may be produced synthetically by methods known in the art, including modification of whole antibodies or synthesis using recombinant DNA methodologies, including using phage display libraries.

As used herein, the term "label" includes a detectable indicator, including but not limited to labels which are soluble or particulate, metallic, organic, or inorganic, and may include radiolabels (such as, e.g., $^{14}$C, $^3$H, $^{32}$P), latex or other beads, enzymatic labels (e.g., horseradish peroxidase, galactosidase, and other enzyme conjugates), spectral labels such as green fluorescent protein, quantum dots, polarimetric spin labels, fluorescent dyes (e.g., fluorescein and its derivatives, e.g., fluorescein isothiocyanate (FITC), Alexa Fluor® 488 Dye, which is a green-fluorescent dyes conjugate with nearly identical spectral properties and quantum yield as fluorescein isothiocyanate, rhodamine, Yo-Pro, a carbocyanine nucleic acid stain sold by Invitrogen, catalog Product V13243, the green-fluorescent YO-PRO®-1), chemiluminescent compounds (e.g., luciferin and luminol), spectral colorimetric labels such as colloidal gold, or carbon particles, or colored glass or plastic (e.g. polystyrene, polypropylene, latex, etc.) beads, as well as dyes, including the cell-permeant pH indicator, carboxy SNARF®-1, an acetoxymethyl ester, acetate which has a pKa of ~7.5 after de-esterification and is sold by Invitrogen, as catalog #PPLM63-C1270. Where necessary or desirable, particle labels can be colored, e.g., by applying dye to particles.

This, the label can be detected using colorimetric platforms with enzyme-produced color like in ELISA type tests.

Luminometers can also be used. Fluorescence polarization can also be used. FRET (fluorescence resonance energy transfer) can also be used.

As used herein, the term "colored particle label" includes, but is not limited to colored latex (polystyrene) particles, metallic (e.g. gold) sols, non-metallic elemental (e.g. Selenium, carbon) sols and dye sols. In one embodiment, a colored particle label is a colored particle that further comprises a member of a conjugate pair. Examples of colored particles that may be used include, but are not limited to, organic polymer latex particles, such as polystyrene latex beads, colloidal gold particles, colloidal sulphur particles, colloidal selenium particles, colloidal barium sulfate particles, colloidal iron sulfate particles, metal iodate particles, silver halide particles, silica particles, colloidal metal (hydrous) oxide particles, colloidal metal sulfide particles, carbon black particles, colloidal lead selenide particles, colloidal cadmium selenide particles, colloidal metal phosphate particles, colloidal metal ferrite particles, any of the above-mentioned colloidal particles coated with organic or inorganic layers, protein or peptide molecules, or liposomes. For example, Quantum dots sold by Invitrogen, is a label encompassed herein.

BRIEF DESCRIPTION OF THE FIGURES

FIG. 23 is an illustration comparing steps of a conventional collection and processing of semen vs use of an assay in accord with the present invention.

FIG. 24 is a schematic correlation of sperm acrosome membrane state to event occurring high in the female tract from Flesch and Gadella (2000).

DETAILED DESCRIPTION OF THE INVENTION

Freshly ejaculated mammalian sperm cannot fertilize, only acquiring that ability upon maturation (Fraser, 2010). With further aging, they become senescent and lose the ability to fertilize, even in vitro (Lechniak et al., 2003). Very few sperm reach the egg to fertilize it, even though in most mammals, many millions of spermatozoa are inseminated to ensure the fertilization of a very few ova. In fact, in one study that attempted to determine the number of human spermatozoa in the fallopian tube after cervical insemination found a median of 251 spermatozoa were recovered (range, 79-1386) 18 hours after insemination (Williams, Hill et al., 1993). These findings lead to the question of how and which sperm are destined to reach the egg.

The changes that enable sperm to fertilize were recognized as early as the 1950s and include sperm maturational changes—some of which are termed capacitation (Chang, 1958; Austin, 1951). Recently, more detailed analysis using proteomics platforms has shown that capacitation is a highly complex process orchestrated by numerous cell surface proteins (Bailey, 2010; Aitken and Baker, 2008; Gadella, 2013).

Later studies have identified sperm attributes associated with normal fertilizing capacity. In a cattle study, it was found that ejaculates that contained a higher percentage of sperm capable of undergoing the acrosome reaction produced higher fertility after intrauterine insemination (Birk et al, 2010). In the human, it was recognized that sperm capable of binding to a specific carbohydrate, hyaluronic acid, produced fewer chromosomal abnormalities in embryos after intracytoplasmic injection of the sperm nucleus into the egg (Huzar et al., 2007). Thus, the state of sperm in an ejaculate affects fertility and embryo health, but no existing method repeatedly monitors changes in the maturity state of sperm prior to insemination and adjusts maturity state to the different ways sperm are applied in assisted reproductive technologies.

In vivo, both the male and female reproductive tracts influence sperm changes as sperm ascend the female tract. But in vitro many of the control mechanisms are absent. The ejaculated spermatozoa are susceptible to the in vitro conditions, where they often are washed, diluted, and certainly exposed to factors that may cause iatrogenic sperm dysfunction (Mortimer, 1991). Therefore, being able to adjust in vitro the state of an ejaculate's sperm to match the type of ART in use can improve outcomes by producing normal pregnancies and healthy offspring.

Figure 2:
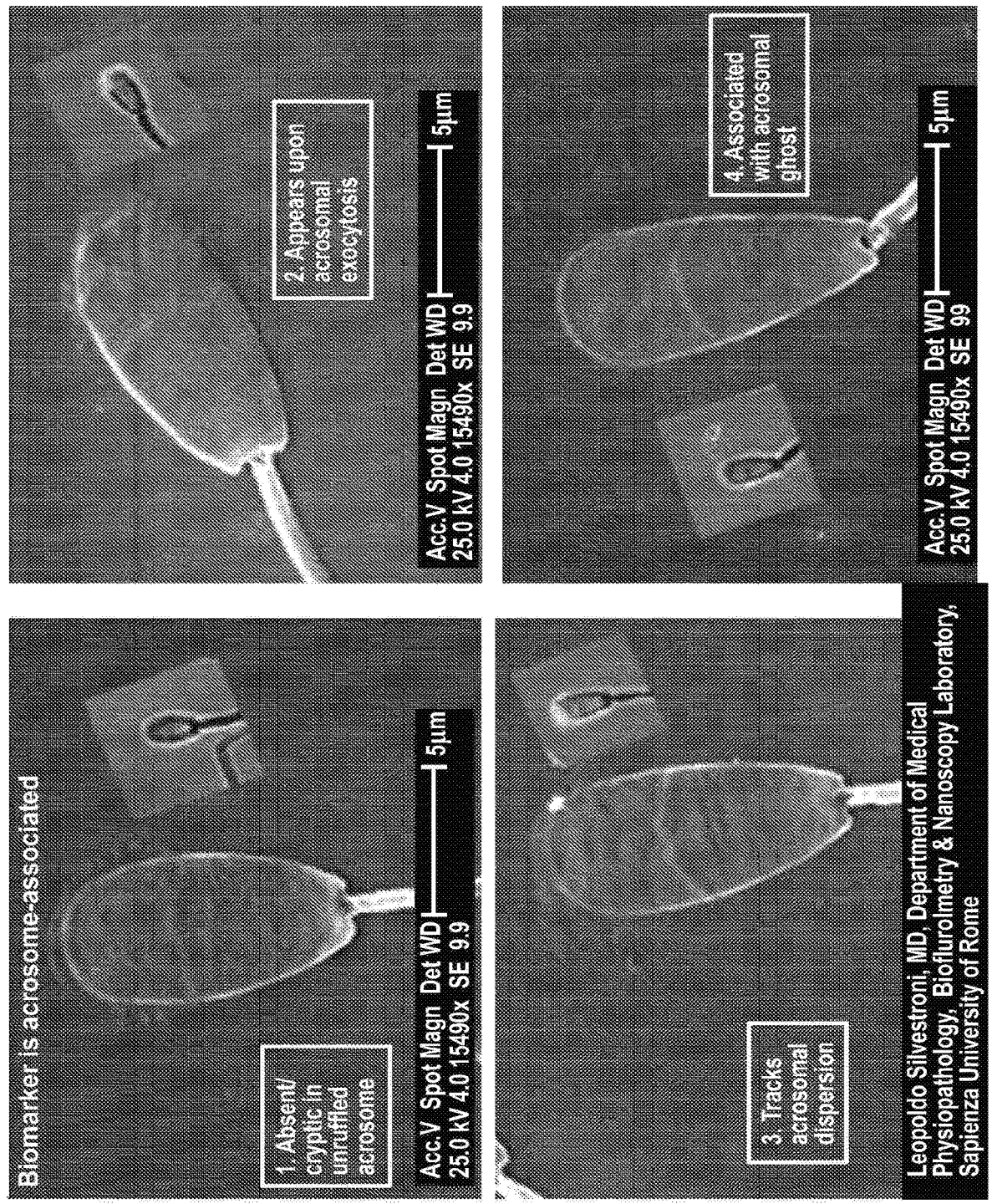
FIG. 2 shows photomicrographs of bull sperm labeled upon assay with the instant invention, showing the different appearance of the most abundant sperm populations at ejaculation (Panel 1) and as sperm are incubated in seminal plasma (Panels 2, 3, 4).
Figure 3:
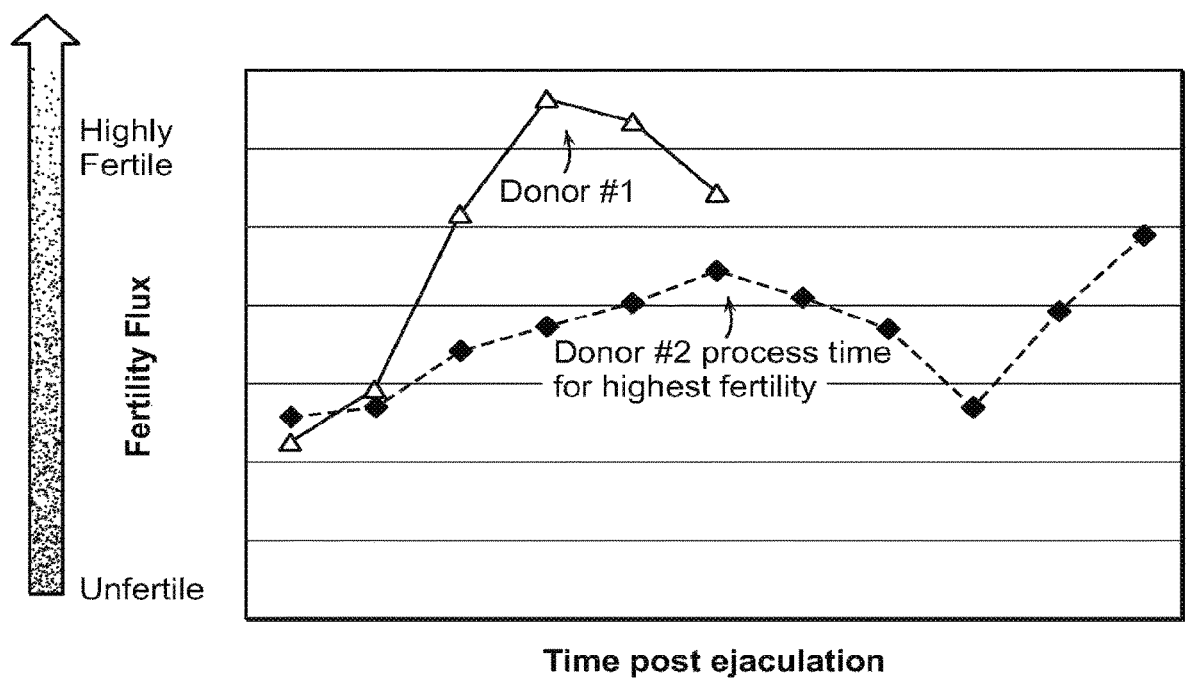
FIG. 3 is a graph illustrating the fertility kinetics of two different ejaculates.
Figure 4:
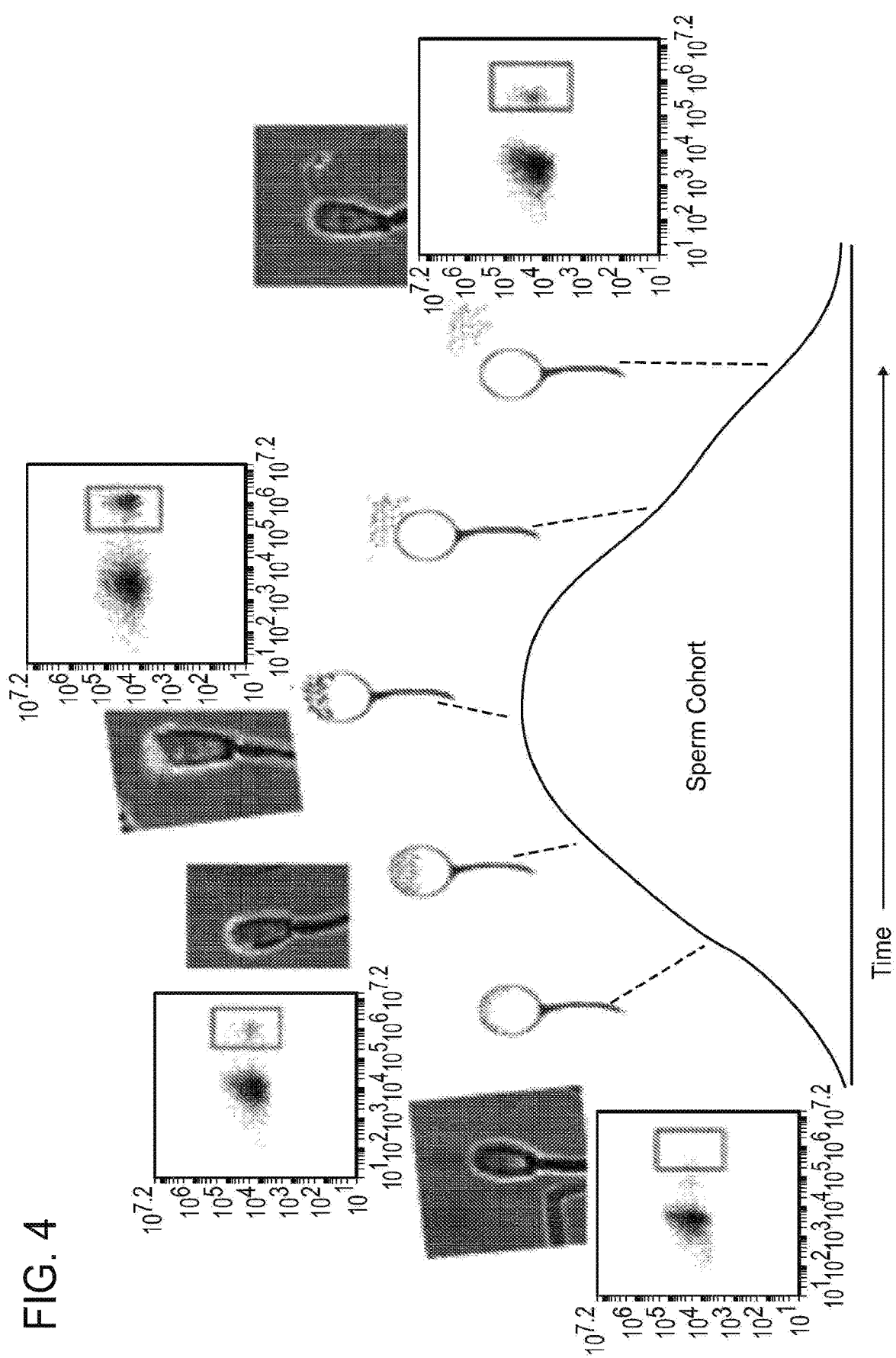
FIG. 4 shows a spectrum of sperm maturation with time, along with images of sperm showing changes that occur with maturation and cytometry plots showing Y-axis (side scatter) vs. X-axis (fluorescence) reflecting the changes that occur in negative and positive sperm pools in an ejaculate as sperm gain fertility (mature) with time, and lose it upon aging.

FIG. 2 illustrates four sperm shown at different stages of marker expression illustrating typical changes that occur with ejaculate maturation. Cytometry plot insets in FIG. 4 show Y-axis (side scatter) and X-axis (fluorescence) and reflect the changes that occur in negative (left) and positive (right) sperm pools in an ejaculate as sperm gain fertility with time, and lose it upon aging. Sometimes in an ejaculate, several cycles of maturation are observed (see FIG. 3, Donor #2).

Collecting the ejaculate is performed generally in accord with conventional procedures. However, preferably the collection device is prewarmed to about body temperature of the mammal from which the ejaculate is collected. After collection, typically the ejaculate is promptly cooled. This is thought to slow down metabolism.

The sperm is then incubated at the cooled temperature by placing the collection device or a container with the ejaculate in a controlled temperature environment, for example, a water bath.

While the ejaculate is incubated, aliquots of the sperm are assayed at intervals to determine the stage of maturation and observe changes in maturation. The closer the intervals for assaying the sperm, the better the results that can be obtained. The time intervals between assaying of aliquots are limited by the time it takes to perform the assay. As seen by data presented herein, assaying at one hour intervals provides significant improvement in fertility and/or gender bias over prior art methods. However, assaying at 30 minute intervals provides better results.

Reagents useful in the present invention include any ligands that can bind to the cell marker or biomarker to provide a detectable result for the real time assay. Many such ligand materials such as, for example, antibodies, lectins, dyes and the like are well known to those skilled in the art. Procedures for binding such ligands depend on the particular Example of suitable reaction buffers (such as Green 1 in examples) include:
Antibody Diluent Buffer (Covance, catalog number SIG-31120), form: Buffer (PBS+0.1% NaN(3)+1% BSA+detergents); and
PBS containing 1 mg/ml BSA Examples of primary ligands (such as Red 2 in examples)—e.g., antibodies or lectins, include: any rabbit polyclonal serum, provided it is produced in such a manner that the Fc region is as normally found in such sera. It is preferred to use antibodies having the Fc region. For example, ChromPure Rabbit F(ab')2 Fragment (Jackson ImmunoResearch cat #011-000-006) typically can fail. In the preferred embodiments of the present assay procedure, it is only necessary for the primary ligand to bind to the sperm cell as it matures (positive reaction). Thus, a typical antibody antigen reaction is not required, unless one desires to follow a specific marker that requires the antibody antigen reaction.

Some examples of such primary ligands include the following, which are dessicated:
Difco Listeria O antiserum type 1 (BD, catalog 223001), sold dessicated but reconstituted as directed on the bottle or by substituting the wash buffer of the instant invention for the water recommended by the manufacturer.
Mouse IgG anti-cloxacillin monoclonal antibody (Charm Sciences)
Mouse IgM anti-calponin (a muscle protein) antibody (developed by the laboratory of Eddie Mabuchi)
ChromPure Rabbit IgG, Fc Fragment (Jackson ImmunoResearch cat #011-000-008)
ChromPure Rabbit IgG, Whole Molecule (Jackson ImmunoResearch cat #011-000-003)
Fluorescein Peanut Agglutinin (a lectin), (Vector Laboratories, catalog FL-1071)
Fluorescein Peanut Agglutinin (a lectin), (Vector Laboratories, catalog FL-1071)—do not need secondary antibody with this reagent
Fluorescein *Pisum Sativim* Agglutinin (a lectin), (Vector Laboratories, catalog FL-1051)—do not need secondary antibody with this reagent
BD Pharmingin™ purified mouse anti-human CD46 (BD Biosciences cat 555948)

Dyes are also suitable for use as a primary ligand. They can provide a detectable signal without the use of a labeled antibody conjugating with them. Examples of suitable dyes that can bind with the sperm cells to observe maturation are FD & C Blue #1 (also called Brilliant Blue FCF), Cell Tracker Red (Life Technologies C34552), Cell Tracker Green Fluorescent Probe (Lonza Cologne GmbH PA-3011 and Hoechst 33342, PE, Cy3, PI, 7-ADD, PE-CY7, FITC (unconjugated) and DRAQ5.

Secondary antibodies (such as Blue 3 in the examples): Any antibody capable of recognizing the first ligand binding to the cell, e.g., a specie from which the first antibody was derived and capable of producing a detectable signal, preferably a fluorescent signal, can be used. Suitable antibodies that provide a detectable signal are well known to those skilled in the art. Some examples include:
Goat anti-rabbi IgG (H+L), DyLight™ 488 Conjugated (Thermo Scientific product #35552)
Alexa Fluor 488 goat anti-mouse IgG (H+L) (Invitrogen A11001)
Alexa Fluor 488 goat anti-mouse IgM (Mu chain) (Invitrogen A21042)
Fluorescein conjugated anti-mouse IgM [rabbit] (Rockland cat 210-4207)
Fluorescein goat anti-rabbi IgG (H+L) (Invitrogen F2765)

Any buffer suitable for washing and resuspending cells can be used. Such buffers are well known to those skilled in the art. Examples of suitable wash and resuspension buffers (such as wash buffer, PBS in the examples) include:

PBS tablets without calcium without magnesium (MP Biomedicals LLC, cat 2810305)

Phosphate buffered saline, 10× solution, Fisher BioReagents (Fisher Scientific cat BP399-500)—used after dilution according to manufacturer Diluents or extenders useful for stabilizing the ejaculate are well known to those skilled in the art. Preferred extenders are those made with milk or egg yolk and a buffer. An example of a preferred extender is BioXcell CSS1 (IMV, code article 018754).

Use of the ejaculate for ART is based on the state of maturation of the sperm cells as determined by the real time assay. For artificial insemination of cows, for example, at the time determined by the real time assay, the ejaculate is processed using conventional techniques. Such conventional techniques include stabilizing the sperm with a diluent and making frozen doses (called straws). As can be seen from the examples and data provided herein, the time for processing can vary depending on whether fertility or gender bias is the desired result. For other ART uses, the time for further processing or actual insemination depends on the state of maturation most closely associated with the state of sperm in a natural insemination process that the ART is replacing or mimicking.

Table 1 compares the embodiments in accord with the present invention with selected published methods that are believed to provide the closest results to the present invention. US 2011/0076667 discloses assay of an ejaculate at multiple points, but differs from the instant invention in both execution and performance. The use of a fixed time of incubating once the disclosed maturational change is detected has now been found to erode performance because, as can be seen from FIG. 5, one cannot extrapolate from the onset of maturation when to further process an ejaculate due to significant variation of maturation of different ejaculates with time. The sperm state of different ejaculates varies too much when processing is initiated at a fixed time from the onset of maturation, a time also referred to as the "jump point" In contrast, processing by using the assay to detect an optimum maturation state at the best time for further processing, determined in accord with the present invention, gives a performance increase.

TABLE 1

Comparison of the Instant Invention and selected Prior Art

| Parameter | Instant Invention | US 2011/0076667 | US 2005/0192266 |
|---|---|---|---|
| Means to improve reproductive Outcome | Assay identifies when to process sperm so that the sperm state reported by assay is immediately captured upon further processing, without extensive biological change | Assay identifies when to initiate a fixed-time incubation prior to processing sperm. The fixed time incubation impairs outcome because sperm state changes differently in different ejaculates during fixed incubation. | Use of a physical sperm separation, after a predetermined incubation as the processing method |
| Means to achieve different desired outcomes | Different methods are used because the sperm states required for fertility and for gender bias differ | The identical method is used for both gender bias and fertility, meaning neither performs well | Gender bias is achieved as described above, fertility is actually damaged by process |
| Means to achieve desired outcome with different methods of ART | Different processing methods are taught for different types of ART | Only intrauterine insemination is taught | Only intrauterine insemination is taught |

It has now been found that the ability to predict sperm state at fixed time after a first jump in population of positive sperm ("the jump point" disclosed in US 2011/0076667) is inconsistent and unreliable. Assay kinetics of sperm maturation in both human subjects and bulls (see FIG. 5) illustrate two points: (1) high variability between ejaculation and development of a positive sperm population, and (2) that it is impossible to obtain the same sperm state in different ejaculates by waiting a fixed time after sperm first become positive.

Figure 5:
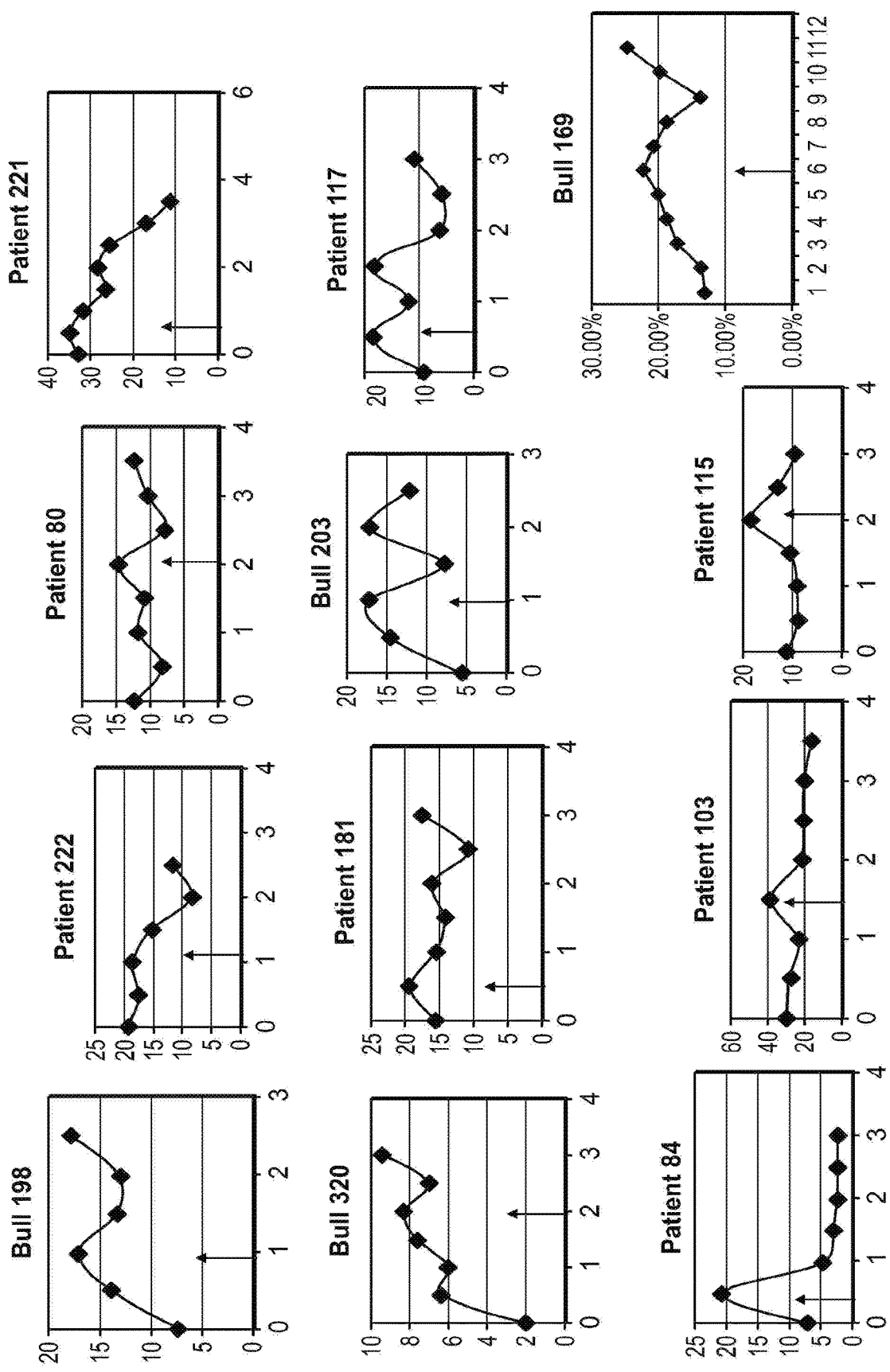
FIG. 5 are graphs illustrating differences in percent maturation vs. time for a number of different ejaculates.

Processes in accord with the present invention allow consistent prediction of optimum sperm maturation for use in ART based on all experimental observations to date (such as illustrated in FIG. 5). Rapid multipoint real time assays in accord with the invention show that, immediately post-ejaculation of normal semen, a low percentage of sperm in the population express the marker being observed by the assay. Applying this monitoring to each ejaculate, it can be seen that the percentage of sperm in the population that express the marker rises, before finally declining. In some cases, the cycle may repeat, which is not shown here. The most important finding is that these changes, as measured by the assay, correlate with fertility. They also correlate with other attributes such as male or female gender bias of offspring.

Figure 6:
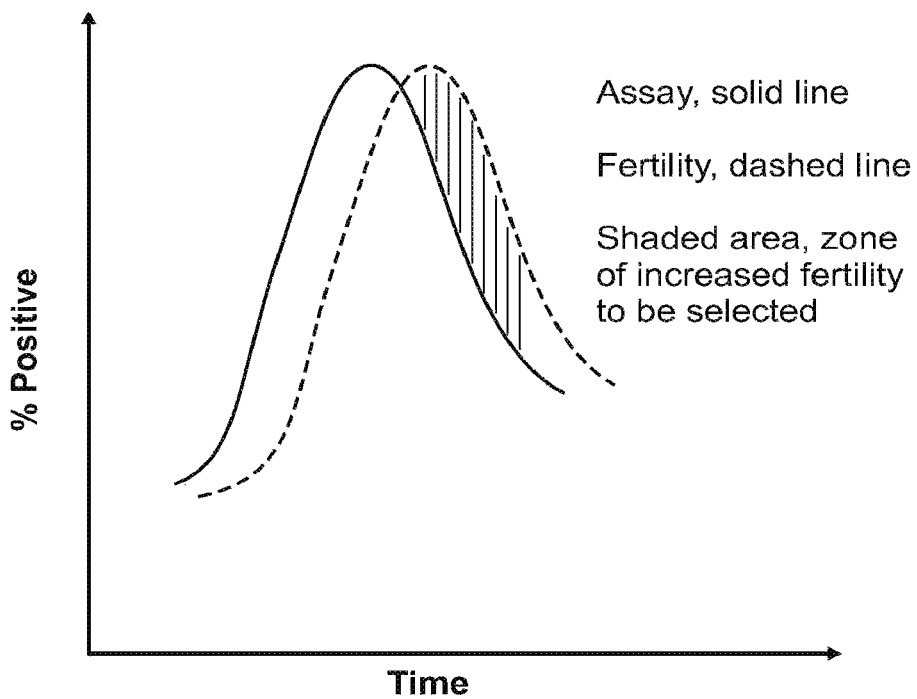
FIG. 6 is a graph illustrating the correlation between assay for sperm maturation marker and predicted fertility based on the maturation state.
Figure 7:
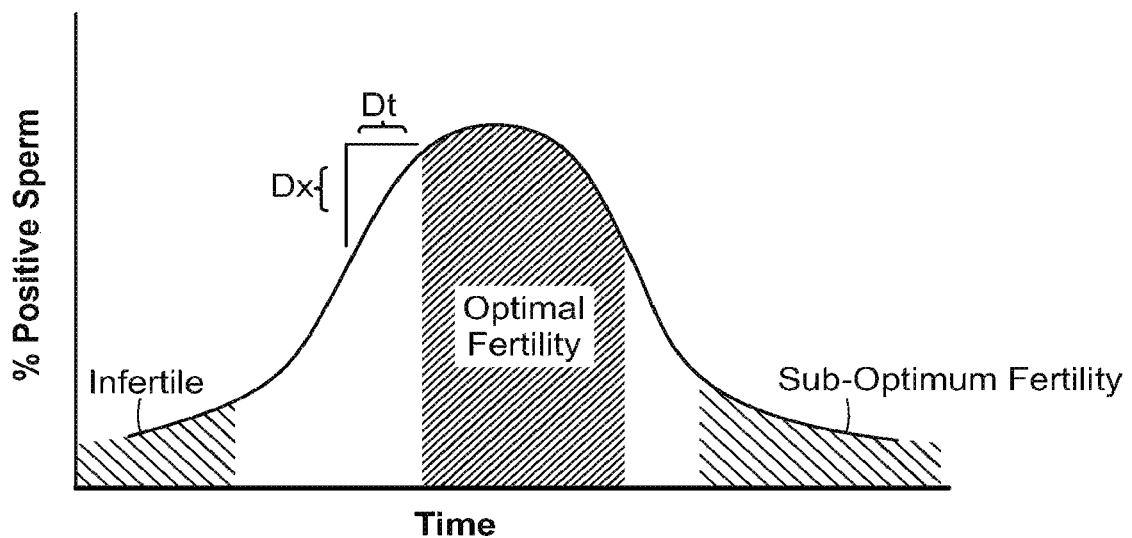
FIG. 7 is a graph illustrating a typical relationship of % positive sperm vs. time and fertility.

The relationship between sperm assay results in accord with the present invention and outcome of intrauterine insemination is illustrated in FIG. 6. The assay shown by solid line correlates to fertility shown by dashed line. Cells become positive before they become fertile, and they remain fertile after the positive population begins to decline. FIG. 7 illustrates how the change in the % positive sperm, d(x), changes over time, d(t), and indicates desired time range for fertility. FIG. 7 illustrates the correlation of gender bias outcome with assay results.

In contrast to prior art methods, processing semen by using a rapid, multipoint, real time assay in accord with the present invention to detect the maturation state at an optimum time for further processing gives a performance increase in percent of births and percent gender bias. How quickly the maturation proceeds after collection, even with cooling, was surprising. It was not anticipated in a biological system cooled to 4-12° C., with the resulting reduction in metabolic rate and slowing of chemical reactions.

Figure 8:
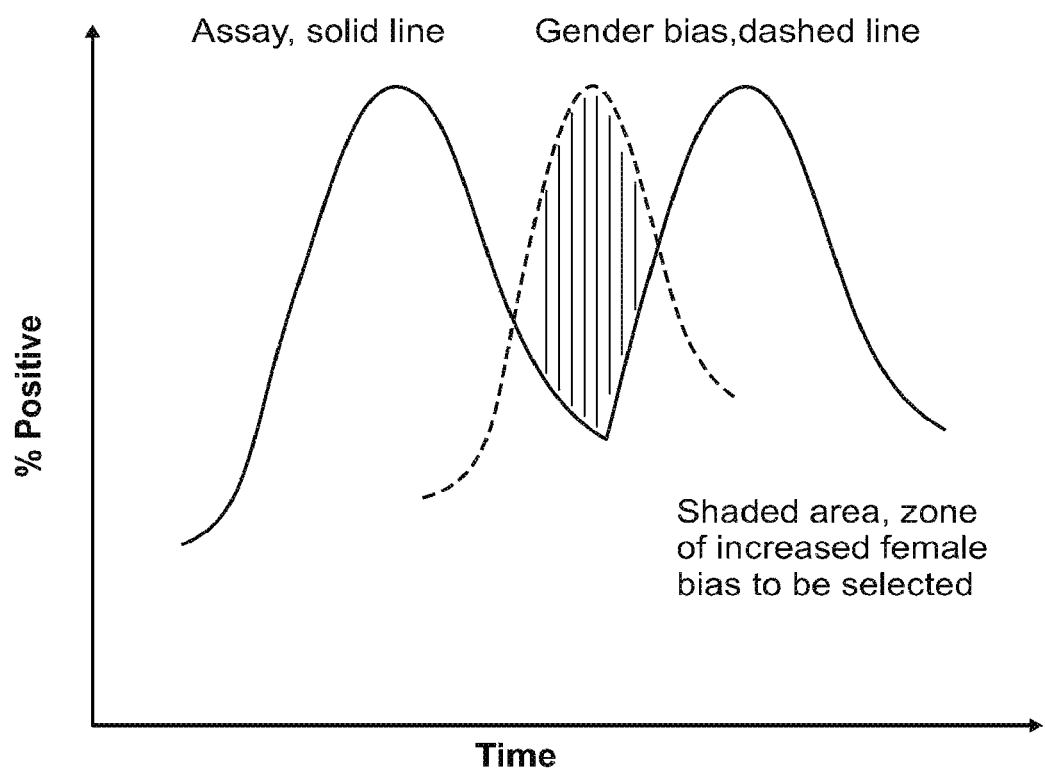
FIG. 8 is a graph illustrating the correlation between assay for sperm maturation marker and predicted female gender bias based on the maturation state.

By optimum time, as used herein, it must be realized that the exact optimum depends on the ability to assay rapidly, and the time between multipoint assays can affect the optimum. However, as seen in FIGS. 6-8, processes in accord with the present invention provide prediction of a period of time during which improved results typically can be obtained when compared to prior art processes.

Figure 1:
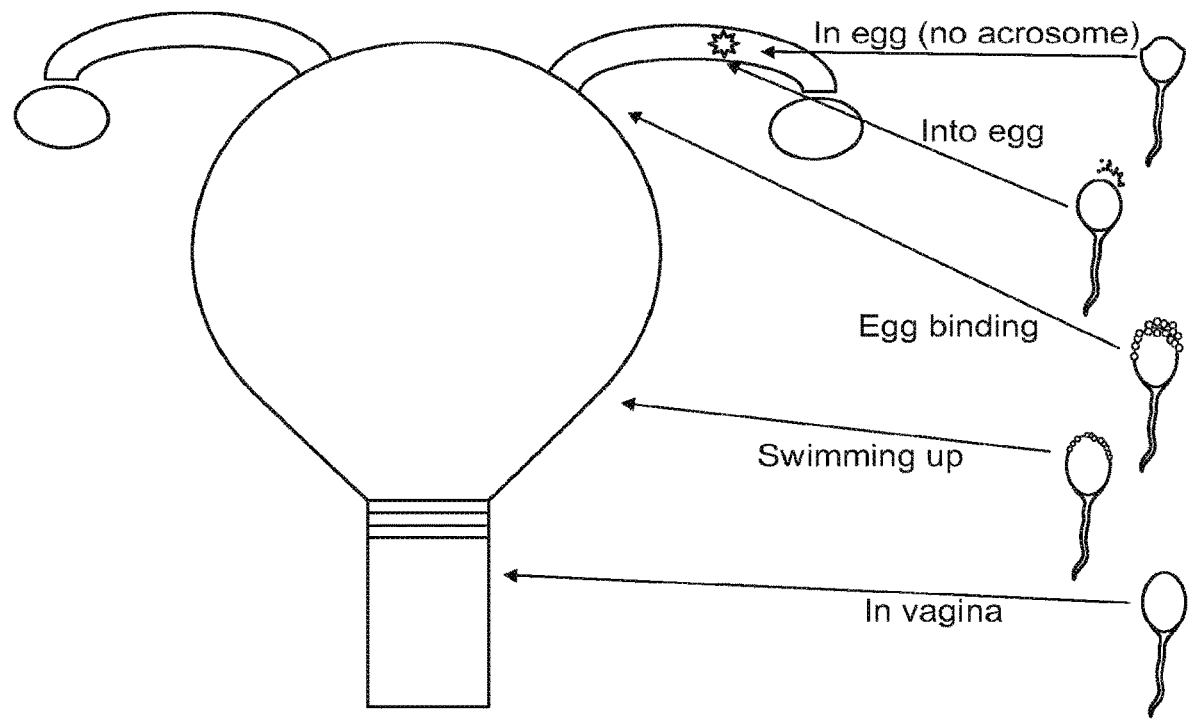
FIG. 1 illustrates a model of time differences as sperm ascend the female reproductive tract.

One preferred embodiment of the invention to process sperm for intrauterine insemination, as described in a following example, has already demonstrated improved pregnancy outcomes in a Phase I clinical trial. In the trial, the sperm fertility state pre-insemination was repeatedly monitored and adjusted to a more mature state than found at ejaculation in natural mating or at collection of semen for ART. Maturation in natural mating is illustrated schematically in FIG. 1. The terms "adjust," "adjusted," "adjustment" and the like, as used herein, mean to allow the sperm to mature to the desired state of maturity, which is an adjustment from the state when ejaculated.

Measurement and adjustment of sperm maturation in vitro to the different states required for the different ways sperm are used in Assisted Reproductive Technologies (ART) is needed to compensate for the differences between ART and natural mating. Measurement includes, for example, monitoring visually by microscope and estimating the percent of sperm exhibiting a marker that correlates with the desired maturity, using cytometry, using video imaging techniques with computer aided analysis, and the like.

Figure 25A:
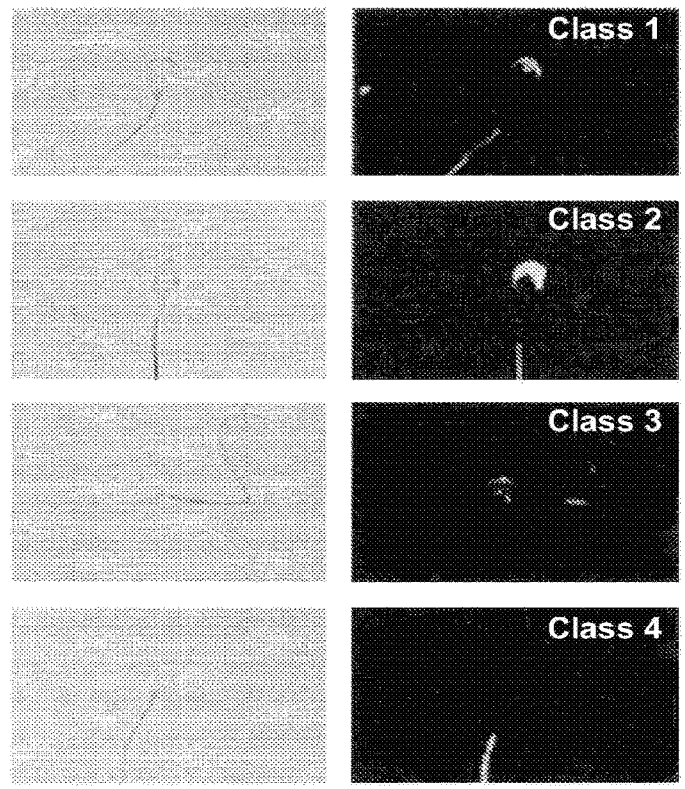
FIGS. 25A and 25B show finer detail of acrosomal exocytosis in a figure from Kim et al. (2001).
Figure 25B:
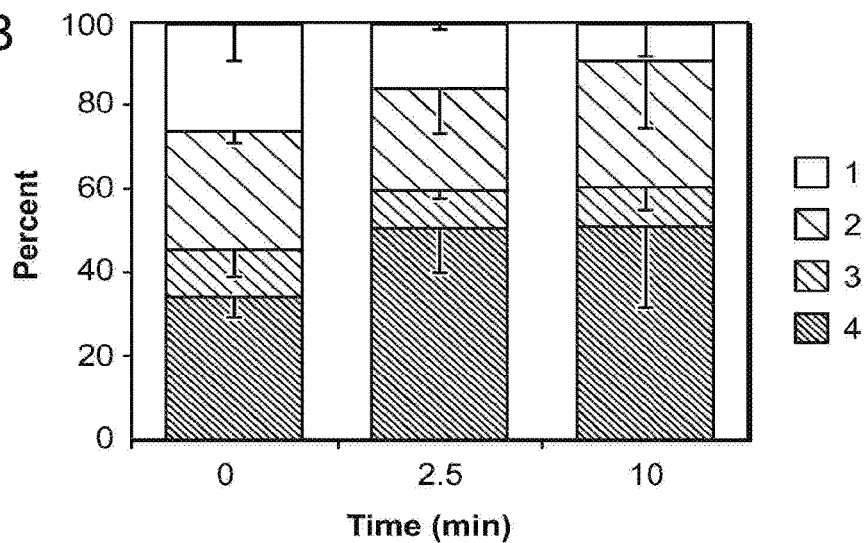

Sperm acrosomal exocytosis is a prolonged event that occurs in stages during maturation. As sperm mature enough to contact the vestments of the egg, they extrude acrosomal contents as shown in FIG. 24, sperm C (from Flesch and Gadella, 2000). Even further along, at the point of penetration, they undergo the acrosome reaction as shown (FIG. 24, sperm D). Acrosome-reacted sperm may be found penetrating the egg vestments as well (Gadella, 2013). Further detail of how the acrosome reaction develops in stages was reported by Kim and colleagues (2001) who state: "Acrosomal matrix proteins remain associated with the sperm for prolonged periods of time following the induction of acrosomal exocytosis, suggesting that transitional acrosomal intermediates may have significant functions in the fertilization process" (Kim et al, 2001). Present Applicant notes particularly the phrase "following the induction of acrosomal exocytosis." Also see FIG. 25, which is reproduced from Kim (2001), showing their identification of multiple stages of acrosomal change. Kim (2001) concludes: "Hypothetically, this process could enable the sperm to maintain adhesion to the zona while moving through it, i.e., the sperm could use the acrosomal matrix-zona pellucida interactions to 'ratchet' through the zona as the acrosomal matrix gradually disintegrates."

A movie of the acrosome reaction of human sperm was also made by Dr. Leopoldo Silverstroni (http://www.youtube.com/watch?v=DBOXRqUrUuY). From microscopic observation of aging ejaculates that the pale areas and pale vesicles that appear from what was originally a smooth dark (and marker negative), it can be observed that acrosome are positive for the biomarker.

Figure 11:
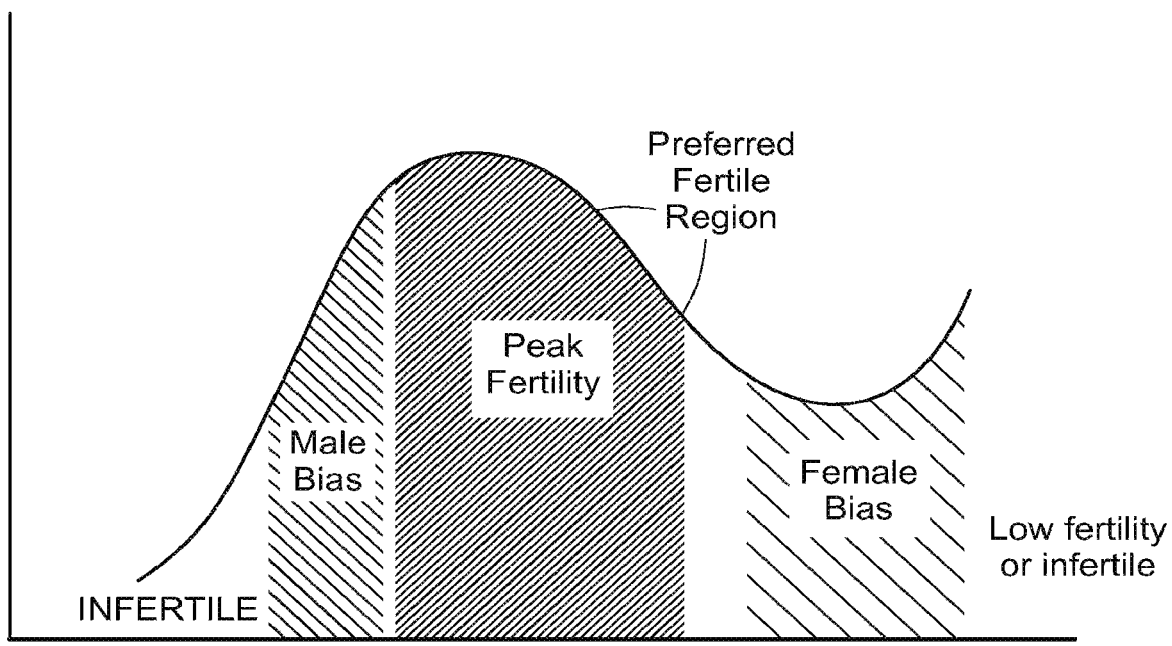
FIG. 11 is a graph like FIG. 10 illustrating a preferred fertile region.
Figure 12:
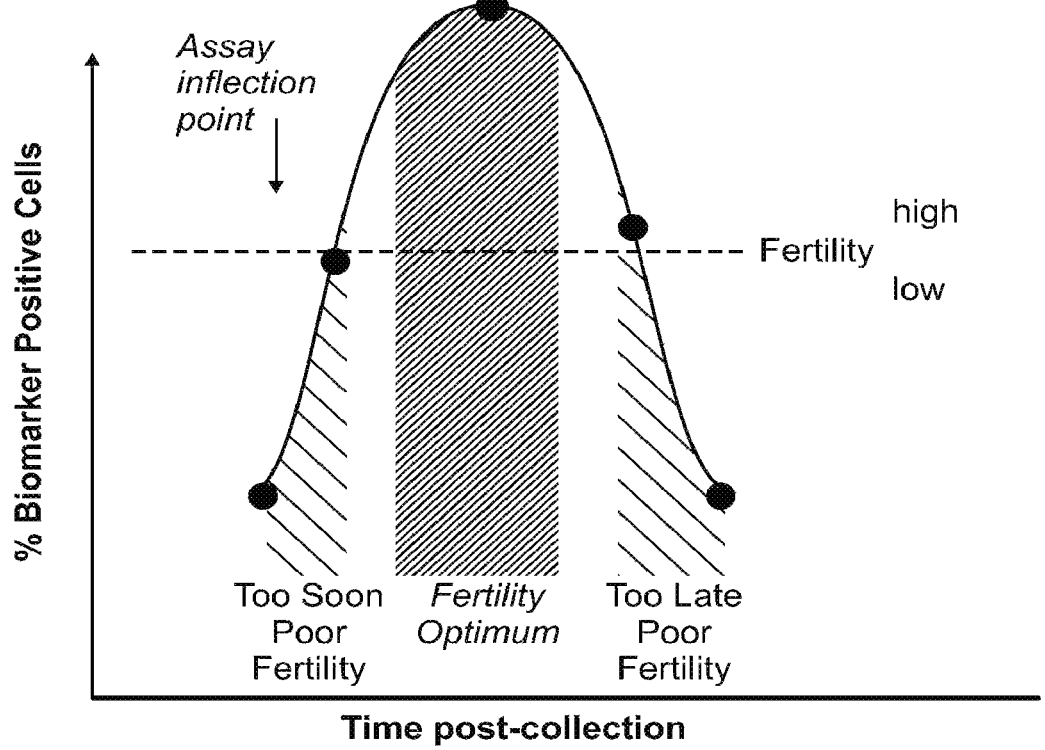
FIG. 12 is a graph illustrating typical expected fertility showing possible assay points for a proposed normal distribution of positive sperm cells vs. time.
Figure 13:
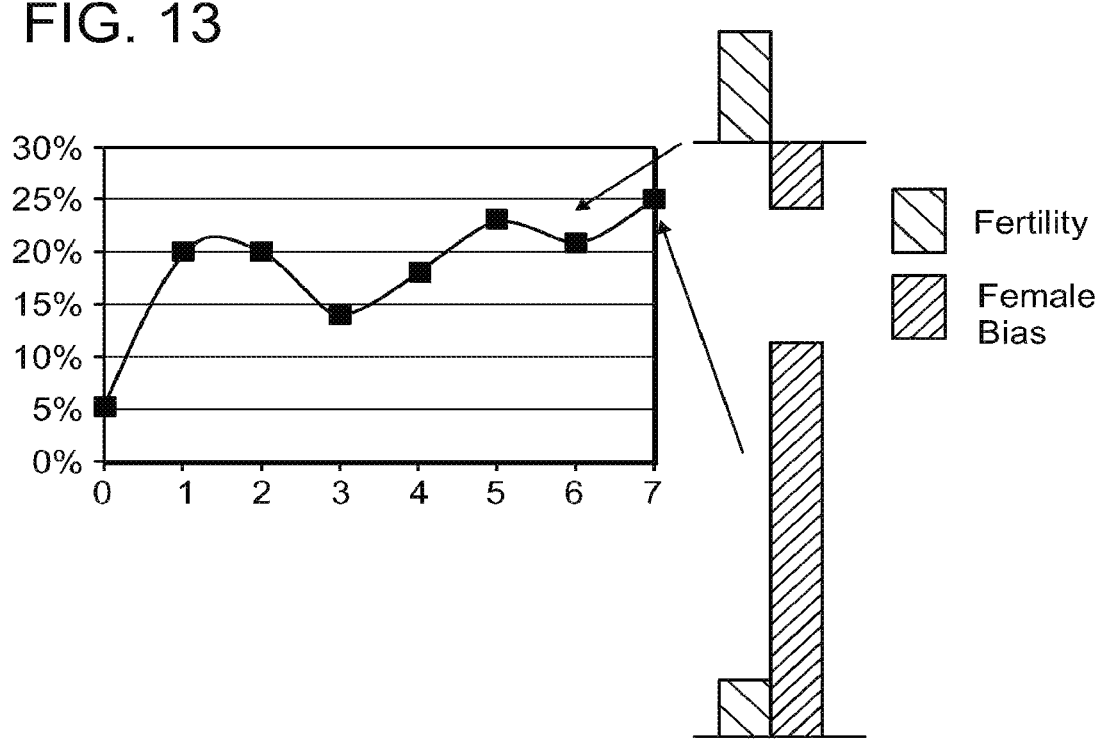
FIG. 13 is a graph of % positive vs time for an ejaculate illustrating results of fertility and female gender bias when inseminated for two different stages of sperm maturation.
Figure 14:
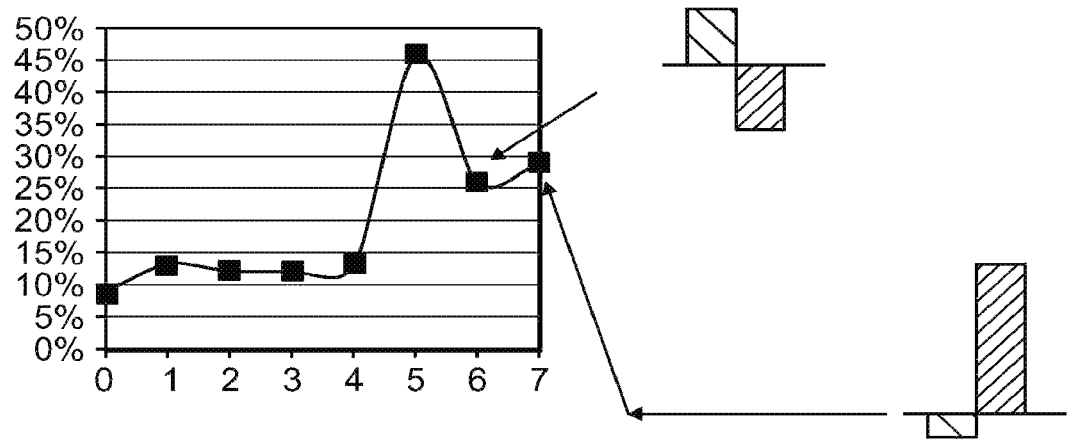
FIG. 14 is a graph of % positive vs time for a different ejaculate illustrating results of fertility and female gender bias when inseminated for two different stages of sperm maturation.
Figure 15:
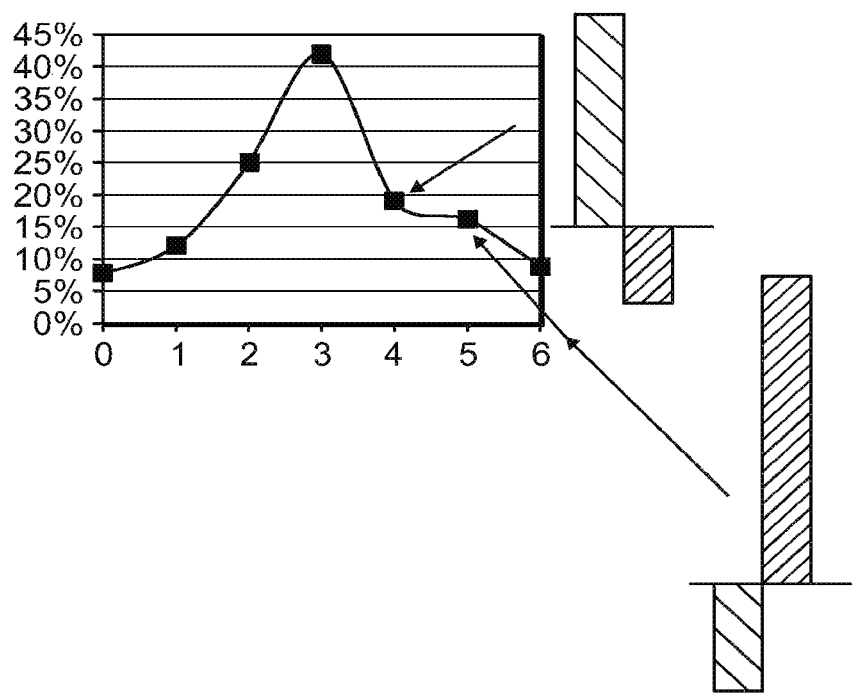
FIG. 15 is a graph of % positive vs time for a different ejaculate illustrating results of fertility and female gender bias when inseminated for two different stages of sperm maturation.
Figure 16:
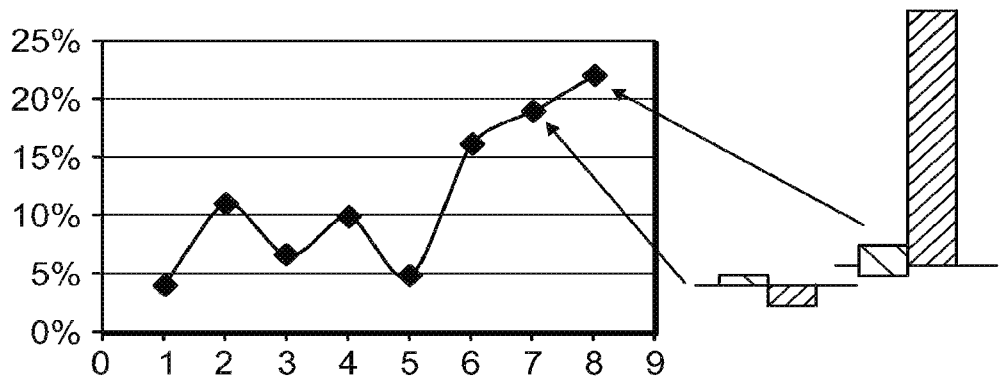
FIG. 16 is a graph of % positive vs time for a different ejaculate illustrating results of fertility and female gender bias when inseminated for two different stages of sperm maturation.
Figure 17:
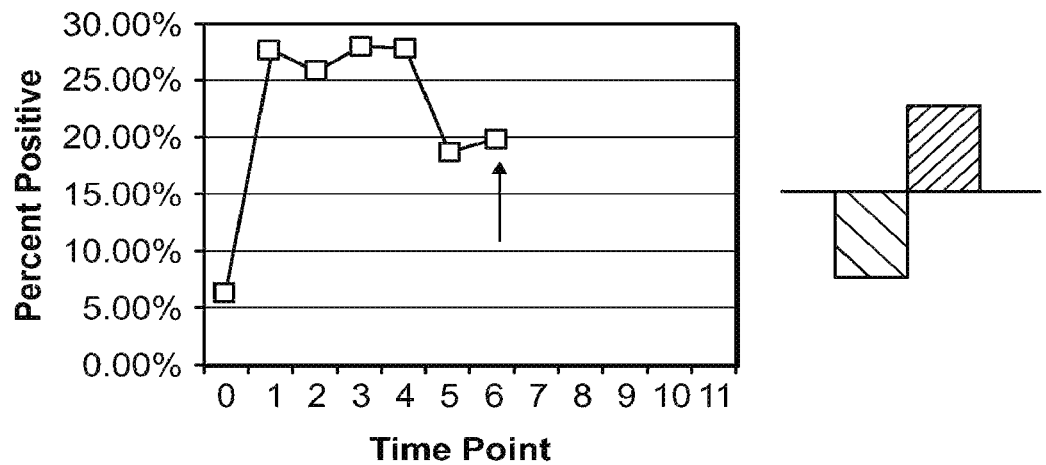
FIG. 17 is a graph of % positive vs time for a different ejaculate illustrating results of fertility and female gender bias when inseminated at the indicated stage of sperm maturation.
Figure 18:
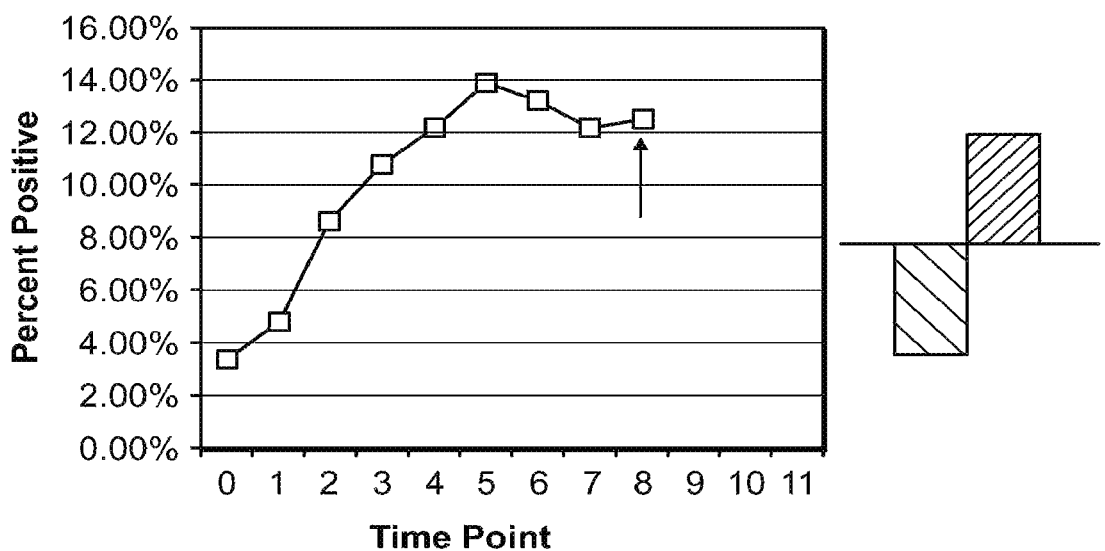
FIG. 18 is a graph of % positive vs time for a different ejaculate illustrating results of fertility and female gender bias when inseminated at the indicated stage of sperm maturation.
Figure 19:
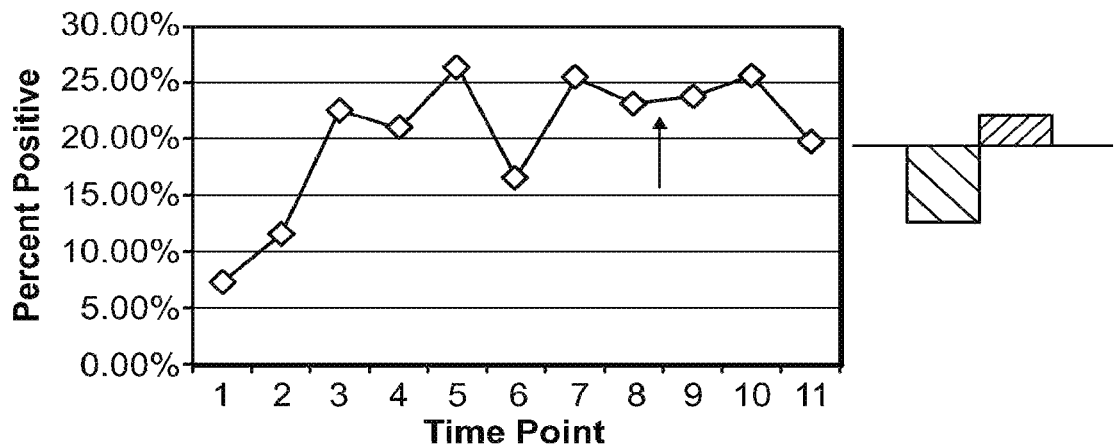
FIG. 19 is a graph of % positive vs time for a different ejaculate illustrating results of fertility and female gender bias when inseminated at the indicated stage of sperm maturation.
Figure 20:
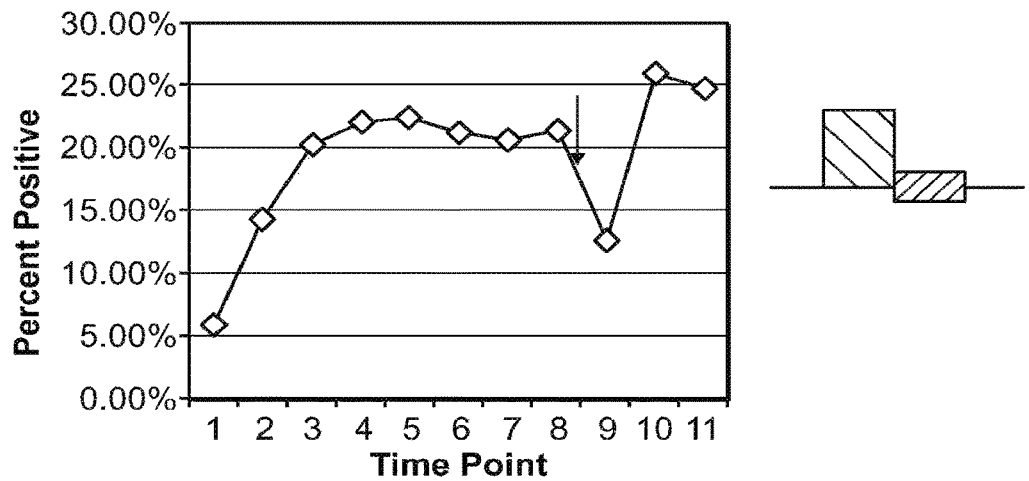
FIG. 20 is a graph of % positive vs time for a different ejaculate illustrating results of fertility and female gender bias when inseminated at the indicated stage of sperm maturation.
Figure 21:
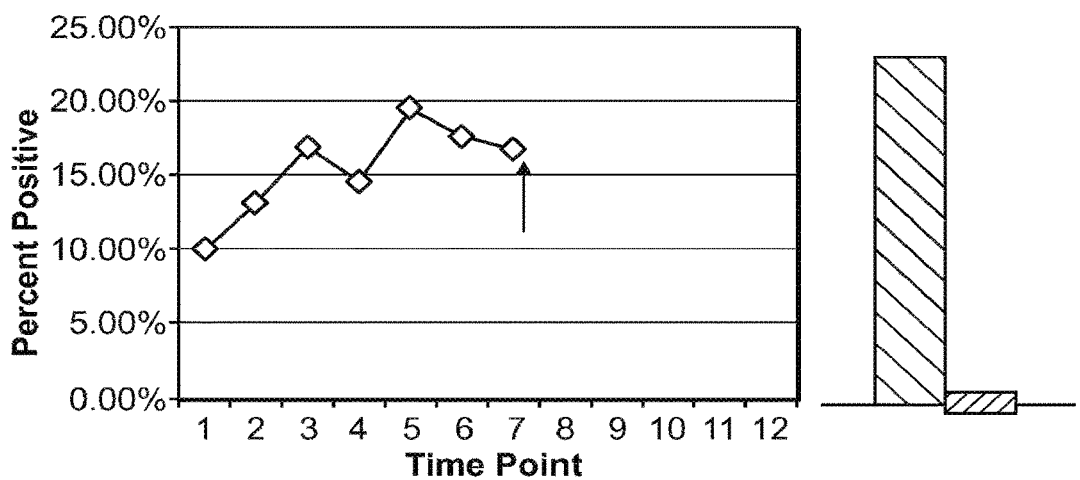
FIG. 21 is a graph of % positive vs time for a different ejaculate illustrating results of fertility and female gender bias when inseminated at the indicated stage of sperm maturation.

Sperm appearance during assay can be correlated to stages reported in the scientific literature. The stages and classes of sperm acrosomal appearance reported in the literature were correlated to the assay curve as follows. During the assay, cells were scored as positive or negative and observations were also made of the finer details of cell structure. It was observed that sperm initially were predominantly negative and showed no staining. Next, staining appeared on the rostrum (top of the sperm head). Then, the label was observed to extend along a larger perimeter of the sperm head, creating the appearance of a thin labeled crescent. Later, the anterior half of the sperm head became labeled. Then the appearance of "bald patches" on the sperm head, devoid of label, began to appear, along with the appearance of marker-positive small vesicles in the ejaculate itself. Sperm that had undergone the acrosome reaction were seen as negative, because as shown the marker segregates with the acrosomal ghost, not the sperm, upon acrosomal loss. These events were correlated to the assay curve as shown in FIG. 11. Sperm appearance by fluorescence microscopy, and the appearance of numerous marker-positive small vesicles in the ejaculate at later times post-ejaculation were recorded and correlated to assay times.

With reference to FIG. 11, the sperm state most suitable for IVF by assay curve is shown in the white region between the region labeled "peak fertility" and the region labeled "female bias." It is possible to extend this region suitable for IVF slightly into the female bias region if desired. The sperm state most suitable for ICSI by assay curve is the region just to the right of the female bias region, but does not extend high up the curve. This is the region where sperm are in the cohort that has just matured—the longest living sperm, the X-bearing ones, are losing the ability to fertilize. Some positivity of the cells is seen due to a new group of sperm beginning to mature, but these are not fertile and will not acrosome-react readily. Thus, if a group of sperm capable of acrosome reacting and having matured to the state able to penetrate an egg is desired, this is the point on the curve to obtain them or to carry out a separation whereby older sperm with bald patches or fully acrosome reacted are found. These separation methods are well known in the art.

The sperm state most suitable for IVF can be identified as follows. Flesch and Gadella (2000) report that sperm actively extruding the acrosomal material are most suited to interact with egg vestments. Kim and colleagues (2001) have provided a finer level of detail about how acrosomal changes occur in a number of stages (see FIG. 25). The changes these scientists report are observed in ejaculates assayed in accord with the present invention. Based on the present assay, one can map the sperm appearance Kim (2001) indicates most useful for egg binding and penetration onto the assay curve. In this way, the sperm states, associated with the curve, that are most suitable for IVF and ICSI can be identified. The time can be identified when sperm have lost some of their label and have "bald patches" on the heads, but are still at a stage where the population retains both X- and Y-active sperm, as the appropriate state on the assay curve for IVF. It is the stage at which marker-positive vesicles appear in the surrounding ejaculate. It is also easily seen as the appearance of a positive subpopulation having distinctly lower fluorescence, as shown previously in cytometric plots.

The sperm state most suitable for ICSI also can be identified. Gianaroli and colleagues (2010) suggest that acrosome-reacted sperm are most suitable for ICSI. Acrosome-reacted sperm are present as sperm mature enough to be capable of undergoing the acrosome reaction upon chemical provocation (such as addition of ionophores) at the very end stages of sperm cohort maturation. These sperm occur based on the present assay procedure as shown in FIG. 11, to the right of the region of the assay curve used to select female bias in IUI. Because only a single sperm is used to inject an egg in ICSI, additional steps of separation or confirmation of acrosomal absence can be coupled with sperm derived at the appropriate state to produce the largest sperm population of the desired type. Separation and confirmation procedures are well known to those skilled in the art.

It can be desirable to alter sperm condition to optimize performance in certain applications such as ART, encapsulation of sperm for AI, and the like. Suitable agents for modulating sperm function include, for example, dibutyryl cAMP, bicarbonate, caffeine, cyclodextrins, pH of buffer, cholesterol-loaded cyclodextrins, BSA, hyaluronan, Heparin and tubal fluid/other female tract fluids or mucins.

Detecting these rapidly changing states with precision is a preferred condition for successful outcome. ART requires sperm in different states because it differs from natural mating, where infertile sperm are ejaculated into the vagina in many mammals. Older, more mature sperm are then subsequently found in the uterus: so for ART using intrauterine insemination, we adjust the maturation state of sperm to a later stage than found immediately post-ejaculation. Sperm do not encounter and bind to the cumulus cells surrounding the egg until they have swum up the fallopian tubes, high in the female tract, where in natural mating sperm are even more mature: for ART involving the direct mixing of sperm and eggs in a Petri dish (in vitro fertilization), we adjust sperm to an even greater maturity. Finally, the sperm most suited for intracytoplasmic sperm injection directly into the egg are ideally the most mature of all, as they should be ready to actually penetrate the egg: we adjust sperm to a very high level of maturation.

Adjustment of sperm state of maturation for use with the type of ART is important to preferred successful outcomes. For example, conventional intrauterine insemination (IUI) of cattle tends to produce more males than natural mating does. In natural mating immature sperm are deposited in the vagina and have a longer journey to the egg (more time to mature), while insemination of cattle into the uterus results in a shorter journey (less time to mature). Because immature sperm traveling from the vagina have a longer time to mature, they have passed through the initial state that favors producing males and are fully fertile and produce no gender bias. In contrast, when these sperm are introduced directly into the uterus by conventional methods, they have a shorter journey, less time to mature, and typically produce a male bias.

For this reason, in accord with the present invention as illustrated in the Examples herein, sperm is adjusted to the same state (as sperm would be in a natural mating process) to produce improved outcomes in different types of ART. This is based on the length of their journey to the egg, because that translates into the time available for maturation when compared to point of introduction by the ART being used. The state of maturation used to produce female bias in intrauterine insemination (IUI) is the same as used to produce unbiased fertility during in vitro fertilization (IVF). This is because the maturation path is longer in IUI than in IVF, since IUI inseminates sperm into the uterus and IVF mixes the sperm directly with eggs. Because of the longer maturation path in IUI sperm are able to mature beyond their fertility peak and are producing gender bias by the time they reach the egg. But when sperm in the same state are immediately presented to the egg in IVF, with no opportunity for further maturation, they will produce good fertility but not gender bias because they have only matured to the point of producing fertility.

In accord with the present invention, scoring methods using cytometry are preferred to produce greater discrimination of sperm state changes. For simplicity when scoring by microscope, the original tool, all positive populations—meaning pools of cells having greater fluorescence than the negative pool—are scored to produce the assay result of % positive cells. For continuity, this method was also applied to cytometry. But with cytometry, it becomes possible to distinguish pools of sperm with different intensity of positivity or other different attributes such as changes in side scatter or forward scatter, and to count large numbers of cells. Thus, it becomes possible to score the assay with greater discrimination of positive pool types, or other pool types, enabling the assay to more precisely reflect sperm state changes. Assay scoring by changes in subpopulations of positive pools is shown in some of the Examples.

Processing by using an assay in accord with the present invention to detect the maturation state at the exact time of further processing gives a performance increase (Table 2). This is due to how quickly the maturation proceeds, which would not be anticipated in a biological system cooled to 4-12° C., with the resulting reduction in metabolic rate and slowing of chemical reactions.

Publications have taught that cool temperatures slow biological processes, for example, reactive oxygen specie (ROS) generation and DNA damage, and that cooling is benign to sperm provided the temperature drop is gradual. In fact, longer exposure to cold prior to freezing has been reported to slightly improve fertility (Foote and Kaproth, 2002). In contrast, while using the present invention, fertility improvement has been found to be much greater in magnitude and independent of the time that elapses between diluting sperm with a protective diluent and freezing the doses of sperm when comparing same-day freezing with freezing after overnight incubation.

An important consideration in carrying out preferred embodiments of this process effectively is the ability to precisely identify the potentially quickly changing state of maturation of the sperm, because the timing of state of maturation changes are different for every ejaculate, and any lag in detecting the desired state of maturation and stabilizing sperm in the desired state allows the maturation to progress beyond what is desirable.

In the following Examples, the following reagents and materials are used: a collection tube device, an SOP for desired ART use, biomarker assay reagents are supplied as three color-coded tubes (Green 1, Red 2 and Blue 3) plus a wash buffer (phosphate buffered saline—"PBS Buffer"). Standard laboratory supplies are required. The reagents and buffer used in the Examples are formulated as follows:

Reagent Green 1:
　Antibody Diluent
　　Life Technologies
　　Part #00-3118, 250 mL
　　Part #003218, 500 mL
Reagent Red 2:
　Difco Salmonella H Antiserum Poly a-z, EN, G, L, Z, and 1 complexes and a-k, r-z, z6, z10, z29 agglutinins
　　Voigt Global Distributors
　　Catalog 224061
Reagent Blue 3:
　Alexa Fluor Goat anti-rabbit IgG (H+L) Secondary Ab
　　Life Technologies
　　(Cat. No. A-1008
PBS Buffer: 8 g NaCl; 0.2 g KCl; 1.44 g $Na_2HPO_4 \cdot 7H_2O$; 0.24 g $KH_2PO_4$; $H_2O$ to 1 liter. pH 7.2
　VWR
　pH 7.2
　Catalog 95062-798
　Fisher
　×1, 1 L
　pH 7.4
　Catalog #R58190001A
　Fisher
　500 Tablets, each makes 100 mL
　pH 7.4
　Catalog #IC-N2810307

Example 1—Collecting the Ejaculate

1. INSPECT DEVICE
　a. Visually inspect device to be used for collecting ejaculate for cracks or damage before using. Use only devices that are intact Any conventional device can be used. A preferred device can be made as described herein (see Device Manufacture) (A purple bead may be placed into device, but does not appear to be necessary.)
2. BRING DEVICE TO OPERATING TEMPERATURE
　a. Place the device in 32° C. water bath for at least 60 minutes. Make sure device is submerged in water up to the cap of the large tube, so the device warms uniformly. Devices may be left in bath overnight for use the next day.
3. PERFORM COLLECTION AND BEGIN INCUBATION
　a. Use standard methods for attachment to an artificial vagina (AV) and for collection of the ejaculate. If device is out of water bath for more than 5 minutes between placement onto AV and collection, remove it from AV and replace with another device from the 32° C. water bath, so the collection temperature remains near 32° C.
　b. Within 1 minute of collection, retrieve device, cap and invert once, then place immediately into 12° C. water bath.
　c. Measure volume after tube has been in the 12° C. bath for at least 15 minutes, in order to minimize temperature changes. Keep tube submerged in water up to the cap of the large tube during the cooling period to ensure a smooth and uniform drop in the temperature of the ejaculate.
4. ASSAY
　a. Follow instructions in the Assay SOP for evaluating cells and carrying out further processing.

Example 2—SOP: Sperm FERTILITY Adjustment Assay for Intrauterine Insemination of Frozen Semen Doses Before running this procedure, be sure that semen is collected and incubated exactly as instructed in the Example 1 SOP to minimize process failures. Take an aliquot of the ejaculate and process using steps 1-4 below.

1. TREAT
　i. Into 1.5 ml tube, pipet the following IMMEDIATELY before use:
　ii. 100 ul GREEN 1
　iii. 20 ul RED 2
　iv. 5 ul BLUE 3
　v. 5 ul neat semen, mix.
　vi. Assay at 30 min intervals. Keep reagents cool at all times.
2. INCUBATE
　a. Place tube at ambient temperature for 20 minutes
3. WASH
　a. Add 1 ml PBS BUFFER at ambient temperature
　b. Microfuge 30 seconds
　c. Carefully remove supernatant with 1 ml pipet.
4. SCORE
　a. Add ~500 ul PBS BUFFER to cell pellet and mix gently to resuspend
　b. FOR CYTOMETER: place aliquot of resuspended cells onto cytometer SIP tube and analyze on a calibrated cytometer using the "Assay" template (see Assay Scoring SOP for further details) to determine the percentage of marker-positive cells.
5. REPEAT ASSAY AT 30 MINUTE INTERVALS TO DETERMINE TIME FOR EXTENSION AND FURTHER COOLING OF EJACULATE
　a. Repeat steps 1-4 until the percentage of marker-positive cells (green fluorescence on head) reaches a maximum and then plateaus or declines. Immediately upon detecting a plateau or decline in the positive population, further process ejaculate as described in step 6. Further explanation: if the kinetic assay function is described as f(x), when the percentage of the positive population is increasing, d(x)/d(t) is positive. At the peak of positivity, d(x)/d(t) equals zero. When the percentage of positive cells begins to decline, d(x)/d(t) is negative. Capturing the sperm state by proceeding to Step 6 when d(x)/d(t) has just become negative improves fertility in IUI. Capturing the sperm state by proceeding to Step 6 when d(x)/d(t) has been negative for some time, or even has just passed through the nadir of the assay curve and just become positive, improves female gender bias outcome in IUI.

6. FURTHER PROCESS EJACULATE
   a. Transfer desired amount of ejaculate to a whirl-pak plastic bag in the 12° C. bath and immediately extend ejaculate by adding a suitable amount of extender previously brought to 12° C., then immediately transfer extended ejaculate to 4° C. cold room. Use the volume of extender appropriate for the ejaculate, based on existing methods of extension in use at your site.
   b. Continue further processing of extended ejaculate into frozen straws using existing methods of further processing in use at your site.

Example 3—SOP: Sperm FEMALE BIAS Adjustment Assay for Intrauterine Insemination of Frozen Semen Doses Before running this procedure, be sure that semen is collected and incubated exactly as instructed in the Example 1 SOP to minimize process failures. Take an aliquot of the ejaculate and process using steps 1-4 below.

1. TREAT
   i. Into 1.5 ml tube, pipet the following IMMEDIATELY before use:
   ii. 100 ul GREEN 1
   iii. 20 ul RED 2
   iv. 5 ul BLUE 3
   v. 5 ul neat semen, mix.
   vi. Assay at 30 min intervals. Keep reagents cool at all times.
2. INCUBATE
   a. Place tube at ambient temperature for 20 minutes
3. WASH
   a. Add 1 ml BUFFER at ambient temperature
   b. Microfuge 30 seconds
   c. Carefully remove supernatant with 1 ml pipet.
4. SCORE
   a. Add ~500 ul BUFFER to cell pellet and mix gently to resuspend
   b. FOR CYTOMETER: place aliquot of resuspended cells onto cytometer SIP tube and analyze on a calibrated cytometer using the "Assay" template (see Assay Scoring SOP for further details) to determine the percentage of marker-positive cells.
5. REPEAT ASSAY AT 30 MINUTE INTERVALS TO DETERMINE TIME FOR EXTENSION AND FURTHER COOLING OF EJACULATE
   a. Repeat steps 1-4 until the percentage of marker-positive cells reaches a maximum and declines for two consecutive readings.
   b. Upon detection of the second consecutive reading showing a decrease, further process ejaculate as described in step 6. Further explanation: if the kinetic assay function is described as f(x), when the percentage of the positive population is increasing, d(x)/d(t) is positive. We wish to allow the maturation to continue. At the peak of positivity, d(x)/d(t) equals zero. We wish to allow the maturation to continue. When the percentage of positive cells begins to decline, d(x)/d(t) is negative. We wish to allow the maturation to continue up to the point where yet a further decrease occurs, or even the greatest decrease and slight rise. Then we use or stabilize sperm doses for later use.
6. FURTHER PROCESS EJACULATE
   a. Transfer desired amount of ejaculate to a whirl-pak plastic bag in the 12° C. bath and immediately extend ejaculate by adding a suitable amount of extender previously brought to 12° C., then immediately transfer extended ejaculate to 4° C. cold room. Use the volume of extender appropriate for the ejaculate, based on existing methods of extension in use at your site.
   b. Continue further processing of extended ejaculate into frozen straws using existing methods of further processing in use at your site.
   It is preferred to begin Step 6 when sperm are in the state indicated by the preferred fertile region as shown on the graph in FIG. 10. The region labeled Female Bias may be used. For the objective of this Example, do not begin Step 6 when sperm are in the states labeled infertile, male bias or peak fertility. If sperm pass through the female bias state before Step 6 is begun, it may be possible to wait for another round of sperm maturation and carry out Step 6 in the indicated region.

Example 4—SOP: Sperm Adjustment Assay for IVF (In Vitro Fertilization)

Before running this procedure, be sure that semen is collected and incubated exactly as instructed in the Example 1 SOP to minimize process failures. Take an aliquot of the ejaculate and process using steps 1-4 below.

1. TREAT
   i. Into 1.5 ml tube, pipet the following IMMEDIATELY before use:
   ii. 100 ul GREEN 1
   iii. 20 ul RED 2
   iv. 5 ul BLUE 3
   v. 5 ul neat semen, mix.
   vi. Assay at 30 min intervals. Keep reagents cool at all times.
2. INCUBATE
   a. Place tube at ambient temperature for 20 minutes
3. WASH
   a. Add 1 ml BUFFER at ambient temperature
   b. Microfuge 30 seconds
   c. Carefully remove supernatant with 1 ml pipet.
4. SCORE
   a. Add ~500 ul BUFFER to cell pellet and mix gently to resuspend
   b. FOR CYTOMETER: place aliquot of resuspended cells onto cytometer SIP tube and analyze on a calibrated cytometer using the "Assay" template (see Assay Scoring SOP for further details) to determine the percentage of marker-positive cells.
5. REPEAT ASSAY AT 30 MINUTE INTERVALS TO DETERMINE TIME FOR EXTENSION AND FURTHER COOLING OF EJACULATE
   a. Repeat steps 1-4 until the percentage of positive sperm reaches a maximum and then, a pool of sperm with intermediate intensity of positive appears (see cytometer plots below for examples). Immediately upon detecting such an appearance of the pool of intermediate intensity of positivity, further process ejaculate as described in step 6.
6. FURTHER PROCESS EJACULATE
   a. Transfer desired amount of ejaculate to a whirl-pak plastic bag in the 12° C. bath and immediately extend ejaculate by adding a suitable amount of extender previously brought to 12° C., then immediately transfer extended ejaculate to 4° C. cold room. Use the volume of extender appropriate for the ejaculate, based on existing methods of extension in use at your site.
b. Continue further processing of extended ejaculate into frozen straws using existing methods of further processing in use at your site.

Example 5—Cytometric Detection of Correct Time for Further Processing

Figure 9:
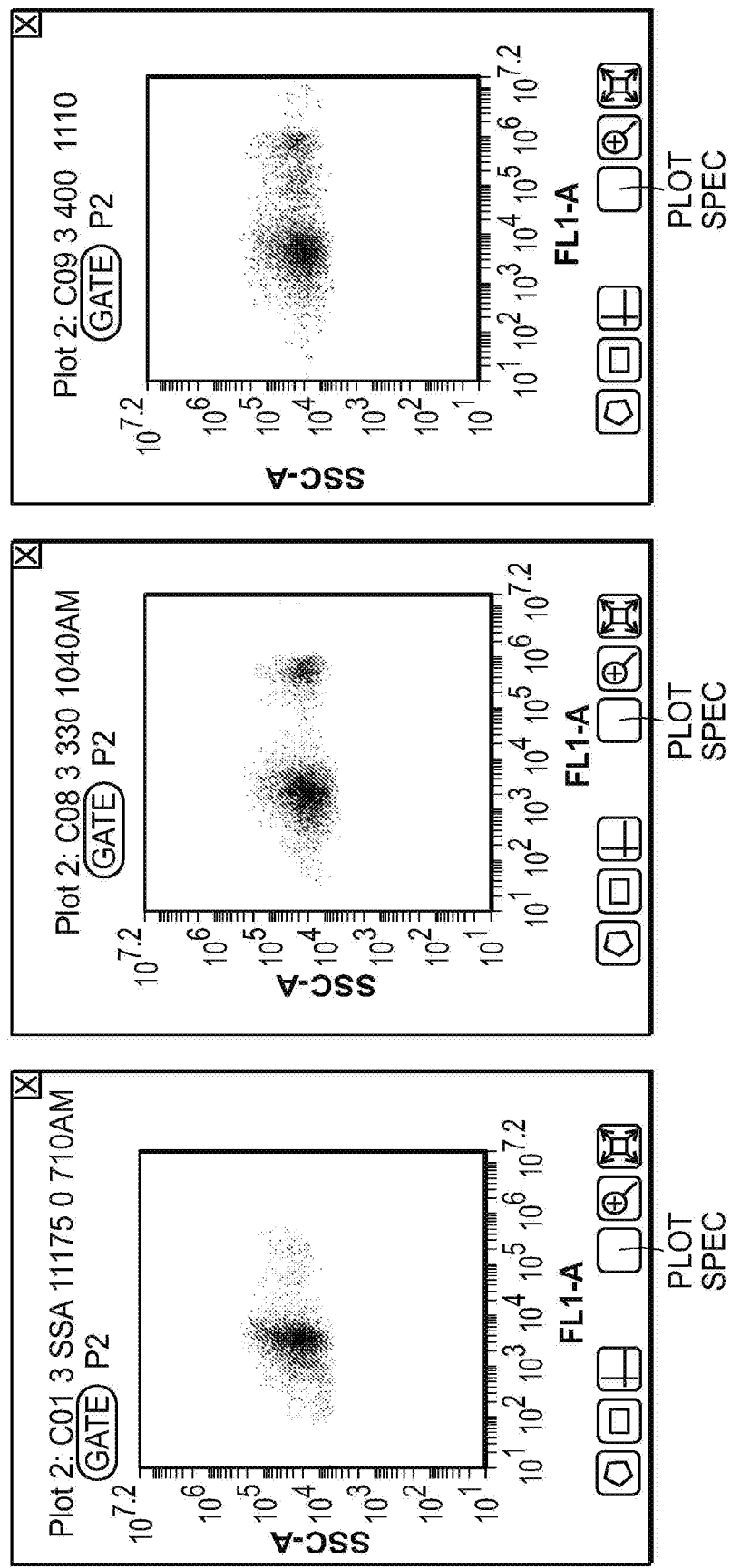
FIG. 9 are images of a cytometer analysis of sperm undergoing maturation at different stages of an assay; negative sperm cluster on left, positive sperm cluster on right.

1. Right after ejaculation, sperm are negative for the marker, and few are found in the positive pool (to the right on the FL1-A axis). See FIG. 9, panel 1.
2. As sperm mature, a positive pool emerges. See FIG. 9, panel 2.
3. With continuing maturation, the cell population in the highly positive pool decreases, and a population of intermediate fluorescence intensity appears. When assay results with this pattern are observed, it is the correct time for further processing (Step 6 in Examples). FIG. 9, panel 3.

Example 6—Collection Device Manufacture

Figure 10:
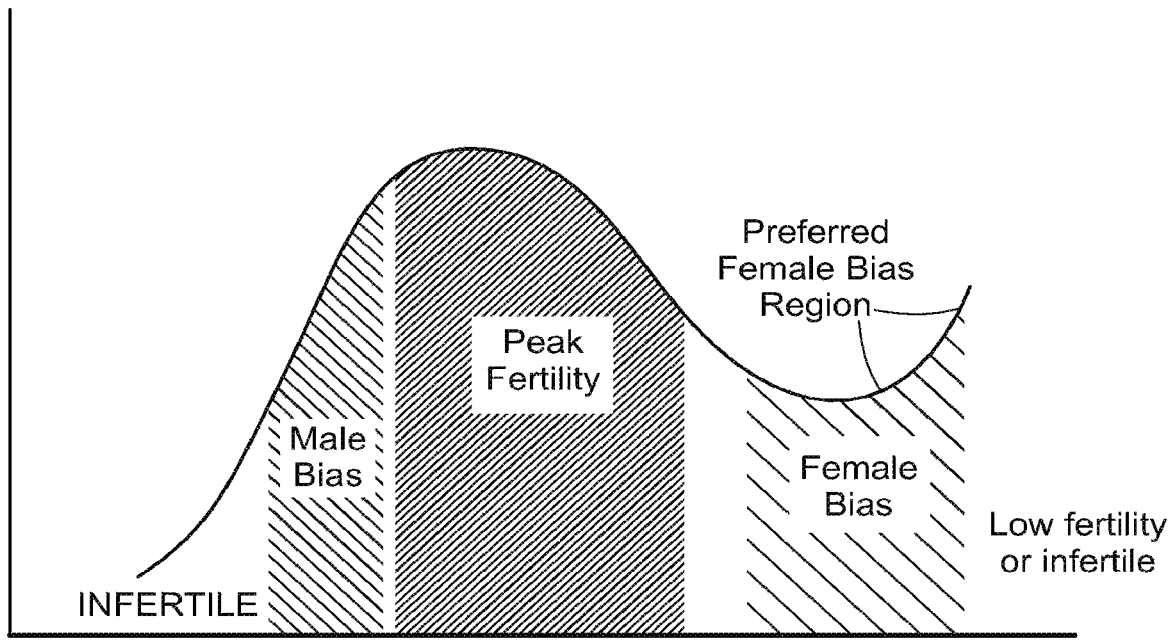
FIG. 10 is a graph illustrating regions of fertility and gender bias for a typical curve of % positive vs time for sperm maturation.

Equipment
Drill Press
Hot glue gun
   Ace Mini-Dual Melt Glue Gun
   Part #2090710
Boring Bit, heavy duty
   Ace Wood, ⅝"
   Part #27531
Jig and clamps
Materials
Lake Charles Manufacturing
   50 mL Polypropylene Centrifuge Tube Molded Graduations without Caps, Non-Sterile—Case 500
   Part #422-0024NC
Caps for 50 mL Centrifuge Tubes
   Lake Charles Manufacturing
   50 mL Centrifuge Tube Screw Cap (Blue)—Case-500
   Part #422-0031
Styrene Inner Collection Tubes
   Lake Charles Manufacturing
   17 mm×100
   207-0004S
Caps for Inner Collection Tubes
   Lake Charles Manufacturing
   Snap Cap
   Part #210-0004
1.5 mL Micro Centrifuge Tubes
   VWR
   Micro centrifuge tube with Big Top attached snap cap
   Part #20170-333
Refrigerant Gel UTEK
   Tegrant Corp
   ThermoSafe
   Utek Refrigerant pack
   Cat #420
   7.5×6, 24 oz. 12/cs.
Chilled Lead Shot #12, 10 lbs
   Ballistic Products
   Cat no. 02612
Glue Sticks
   Ace Glue Sticks, Dual Temperature
   24/Pack
   Part #2013605
Sparkleen
   Fisherbrand scientific
   cat #04-320-4 from
   Fisher Scientific
Device
I. Cap Preparation
   1. Insert ⅝" drill bit in chuck.
   2. Place the jig on the drill press table. Center the jig below the drill and secure in place using the spring clamps
   3. Place the cap open side up on the jig
   4. Press down on the cap against the sandpaper to immobilize the cap
   5. Drill the cap
   6. Clear the jig with compressed air as needed
II. Inner Tube Assembly
   1. Using a fine point permanent marker (Sharpie), highlight the volume divisions on a 15 mL styrene round bottom tube by mL. The 1 mL mark on the tube is labeled as 0 to compensate for the volume of the bead. Number the divisions every 2 mL to the top of the tube
   2. Cut the lid off the 1.5 mL centrifuge tubes. Fill with lead shot to 2-3 mm below the top of tube. With the glue gun set to high, cover the shot. Allow to cool.
   3. Place the styrene tube upside down on a level surface. With the glue gun set on low, soften the glue on the lead filled centrifuge tube. Center the weighted centrifuge tube on the rounded bottom of the styrene tube. The glue will set in about 30 sec.
   4. Push the inner tube assembly, shot first, through the top of the drilled 50 mL cap to the top of the cap. The top of the inner tube extends to about 1 cm from the top of the drilled 50 mL cap.
III. Final Assembly of Device
   1. Place 50 mL centrifuge tubes in the wire rack so that the tubes are tilted.
   2. Fill the tubes to the 35 mL mark with Utek gel. This is best done by a continuous slow addition to the tubes which minimizes the inclusions of bubbles. Use a disposable pipet to remove large bubbles from the gel. Use the 3 mL syringe to adjust the gel volume.
   3. With a twisting motion, seat the inner tube assembly into the gel tube. Screw the cap onto the gel tube, make sure the shot tube is touching the bottom. Twist the inner tube so that the graduations are visible. Tighten cap.
   4. Seal the styrene tube to the cap. With the glue gun on high, slowly make a bead of glue around the styrene tube.
   5. Label the device.
IV. Wash Purple Beads
   1. Add 1 mL detergent into a 250 mL beaker. Add hot water and dissolve powder.
   2. Add up to 20 beads. Swirl occasionally during 1-2 hr soaking.
   3. Rinse the beads with tap water, draining and refilling the beaker. Allow to sit for 20 min.
   4. Rinse ×2 with distilled water. Allow to sit for 20 min.
   5. Dry on paper towels Example 7—Field Experiments Reproductive outcome relates to sperm state by assay, not to elapsed time after semen collection. A number of Holstein bull ejaculates were processed by assay and frozen into doses used to inseminate cows on dairy farms. In some cases, the same ejaculate was split for processing at two different assay states (FIGS. 13-21). Fertility and gender bias outcomes were determined by the methods described in Example 3. Outcomes are consistent with observations that relate assay result to reproductive outcome (FIGS. 10-11).

No relationship exists between time of processing and outcome, but a relationship does exist between the selected sperm assay state and outcome. Selection of a state closer to the development of positivity (FIG. 11) produces better fertility without female gender bias, selection farther from that point (FIG. 10) increases female gender bias but may or may not reduce fertility.

Dairy bull semen was processed as described in Examples 2 or 3 for Fertility or Female Bias for intrauterine insemination of cattle, except that sperm were scored by microscopy and assay was run at hourly intervals. Semen was used in field trials on dairy farms. Reproductive outcome was evaluated by non-return rate (NRR; number of cows not returned for repeat insemination) or by calf sex at birth. With conventional semen, at the time of these inseminations, the NRR for bull fertility was ~68.56 for a bull supplying ~90% of inseminations and 71.75% for a bull supplying ~10% of inseminations. Conventional semen female bias was 48%.

TABLE 2

Increase in Female Calves and Fertility from Sperm Maturation State-based Semen (hourly assays)

| Assay Method | # Inseminations | Fertility (NRR) | # Births | % Female Calves | Change in Fertility | Change from Control Female Calvings |
|---|---|---|---|---|---|---|
| Fertility | 347 | 73.20 | 149 | 45 | +6% | −7% |
| Female Bias | 284 | 71.13 | 148 | 87 | +4% | +23% |

It is difficult and slow to score so many sperm by microscopy! Hourly intervals are required between assay points. And because the biology changes so fast, precision is harder to obtain. Use of cytometry is faster, easier and allows 30 minute assay intervals, as shown below.

Dairy bull semen was processed as described in the attached SOPs for Fertility or Female Bias upon intrauterine insemination of cattle, and used on dairy farms. Reproductive outcome was evaluated by actual conception rate for fertility. Control fertility was obtained from the same farm and inseminator for the preceding 6 weeks of inseminations to conventional semen doses. For gender bias prediction, semen doses were subjected to a swim up procedure followed by digital PCR to detect the ratio of X- and Y-chromosome specific DNA (hence X- to Y-sperm) in the total and motile sperm fractions, allowing prediction of sex bias at birth.

TABLE 3

Increase in Female Calves and Fertility from Sperm Maturation State-based Semen (assay at 30 minute intervals)

| Assay Method | # Inseminations | Conception Rate | Change in Fertility | Female bias Predicted by PCR |
|---|---|---|---|---|
| Fertility | 80 | 48% | +17% | none |
| Female Bias | 138 | 38% | −7% | High |
| Control | 276 | 41% | 0% | none |

Example 8—Correlation Between Assay and Predictors of Improved Human Fertility

Figure 22:
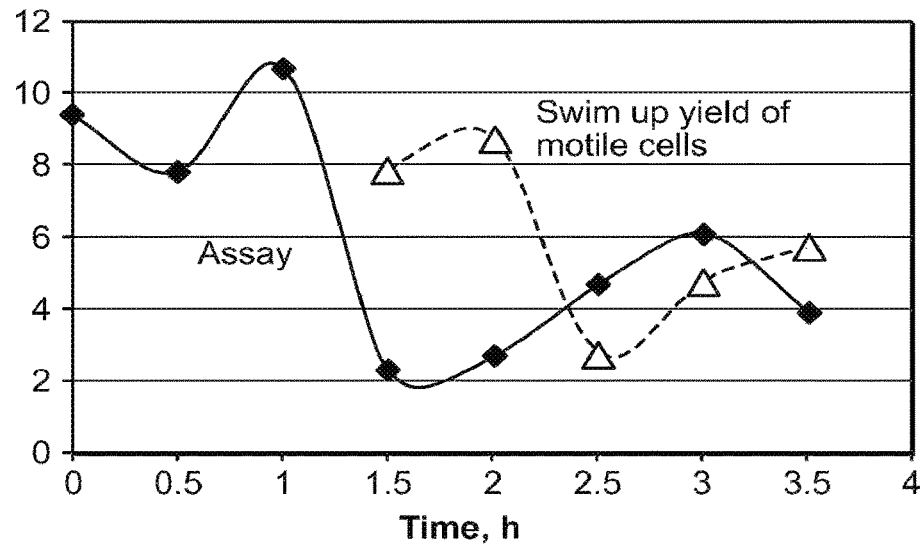
FIG. 22 is a graph illustrating a comparison of results of assay of biomarker for maturation with those of a swim up motility yield.

The assay process in accord with the present invention correlates with known predictors of human fertility (FIG. 22). An ejaculate from a normal donor was processed in the fresh state by assay and at each assay point after the ejaculate had liquefied by a swim up procedure. (Human ejaculates coagulate upon ejaculation and quickly liquefy.) Note out-of phase sinusoidal correlation of the fluctuation in % positive sperm and number of motile sperm. Swim up yield has been shown to correlate with fertility (Shojaei et al., 2012).

Human sperm assay results correlate (out of sinusoidal phase) with predictors of improved fertility, as shown in FIG. 22. The swim up yield fluctuates, suggesting ejaculate fertility does as well.

Example 9—Use of Assay as a Fertility Diagnostic

Ejaculates from 5 bulls were split into a conventionally-processed half and a fertility assay-processed half, to mimic within the same ejaculate doses expected to have lower fertility or higher fertility, as seen from data in Example 7. Frozen doses were blinded and sent for analysis by assay in accord with the present invention (Example 2) to determine whether it is possible to use the assay to distinguish frozen semen doses of lower fertility from those having higher fertility.

TABLE 4

Use of Assay as a Fertility Diagnostic: Assay Distinguishes Ejaculates of High and Low Fertility

| Male Producing Ejaculate | Sample Type | Diagnostic Fertility Score |
|---|---|---|
| Male 1 | Low fertility | Poor |
|  | High fertility | Good |
| Male 2 | Low fertility | Poor |
|  | High fertility | Good |
| Male 3 | Low fertility | Poor |
|  | High fertility | Good |
| Male 4 | Low fertility | Poor |
|  | High fertility | Good |
| Male 5 | Low fertility | Poor |
|  | High fertility | Good |
| Diagnostic Congruence with Expected Result |  | 10/10 (100%) |

Example 10—Comparison of Present Invention with Prior Art

The procedure for the assay in Example 2 was compared to the "jump point" procedure described in US 2011/0076667, which is considered to be the closest prior art. The fertility of both procedures was compared to fertility of conventional procedure performed without an assay. The results are illustrated in the Table 5 below.

TABLE 5

Instant Invention Produces 283% Improvement Over Closest Prior Art in Fertility

| Method of Semen Processing | Number of Inseminations | % Increase in Fertility Over Conventional | Fertility Improvement by Instant Invention |
|---|---|---|---|
| Instant Invention | 80 | +17 | +283% |
| Jump Point Assay (with lag step) | 347 | +6 | — |

Another comparison was made between the procedure for the assay in Example 2 and the "jump point" procedure described in US 2011/0076667. The results are illustrated in the Table below. This time, the improvement over the "jump point" procedure was not as dramatic, but still quite significant. See Table 6 below.

TABLE 6

Instant Invention Produces 84% Improvement Over Closest Prior Art

| Method of Semen Processing | Number of Inseminations | % Increase in Female Calvings | Improvement by Instant Invention |
|---|---|---|---|
| Instant Invention | 284 | 23.0 | +84% |
| Jump Point Assay (with lag step) | 3,600 | 12.5 | — |

Thus, real time assays in accord with the present invention are useful for industrial semen processing for agriculture. These procedures can be used to identify and maximize the fertilizing capacity of sperm. In a non-limiting example of reduction to practice, a bovine ejaculate is collected into a device designed to buffer semen temperature changes and provide more precise temperature control to maintain sperm integrity (see Examples). The ejaculate is subject to controlled cooling and preferably is assayed at 30 min intervals for changes in percent positive sperm in the population.

In bovine semen processing, ideally an artificial vagina (collection device) is prewarmed to the temperature of cattle, preferably about 38° C. or slightly more to compensate for cooling between removal from the heating box and semen collection. Cooling of sperm too abruptly after collection causes cold shock and results in curling of the sperm tails. For human collections, ambient clinic temperature is used. A preferred device for containing bovine ejaculate has high thermal capacity and preferably is prewarmed in a range of temperatures from ambient to 40° C. depending on the mammal but, for bovine, preferably in a range of about 32-38° C.

After collection, standard processing methods may keep semen warm initially and then cool it, or simply place the collection at ambient lab temperature. For bovine semen, preferably cooling is immediately initiated. For example, the time required for cooling a bovine ejaculate to 12° C. in a recirculating water bath set at 12° C. is about 20 minutes. For a human ejaculate, cooling preferably is slightly slower, about 40 minutes. Regarding range of cooling, it is possible to run the assay on room temperature collections, that are not cooled, but the assay signal is often lower and recalibration of the assay may be required to identify appropriate states. Those skilled in the art can readily determine the best cooling procedure for specific mammals by routine methods.

The fastest rate of cooling is limited by sperm damage due to cold shock. For example, immediately cooling an ejaculate in the cattle collection device in a 4° C. water bath damages the sperm. The rate of cooling is adjusted by bath temperature. The range of bath temperatures can be from the temperature that does not produce cold shock in sperm, which is above about 4° C., up to the temperature that would not produce heat shock in sperm, above about 40° C. Typically, the desired range of bath temperature is from about 4 to 12° C., more preferably from 6 to 12° C. The most preferred temperature range is about 12° C.

Sperm can be incubated at a temperature that ranges from just low enough to prevent heat shock, i.e., about 40° C., to just high enough to prevent cold shock, i.e., just above 4° C. Preferably, sperm are incubated at temperatures ranging from ambient of about 25° C. to just above about 4° C. More preferably, sperm are incubated in a temperature range from about 12° C. to just above about 4° C. With more gradual cooling, it becomes possible to incubate sperm from just above the freezing temperature of an ejaculate, where nucleation of ice crystals occurs, to the upper temperature ranges stated.

The assay can be run using a number of different reagents to create a signal, as has been previously disclosed. Examples of useful reagents are disclosed in this application. For the buffer in which the reaction is run, a range of buffers is suitable, although those buffers that contain agents to stabilize antibodies, especially bovine serum albumin, in the commercially sold formulations are preferred. Preferably, the assay is run using a primary antibody and a secondary antibody that is labeled with a fluorescent label. A primary antibody consisting solely of the Fc region can be used. Polyclonal or monoclonal antibodies can be used, preferentially from mouse or rabbit. For the secondary antibody, which must recognize the antibodies from the animal or human species of the primary antibody, the label used preferably can be detectable by cytometry. Preferentially, the label of FITC or AlexaFluor 488 is used. The assay wash buffer and the buffer in which sperm are resuspended for measurement of the positive population can be drawn from those buffers normally used in washing of cells, such as isotonic phosphate buffered saline at pH 7. Preferably, the same buffer is used for both purposes.

Assay reagents should be mixed immediately before the assay is run. Mixing reagents more than 5 to 10 minutes before the assay is run in the absence of sperm can reduce signal intensity. Mixing reagents and sperm more than 5 to 10 minutes before assay incubation will affect the final sperm state that is detected and is undesirable. The incubation time for the assay preferably is short, but will depend on the reagents being used. An incubation time in the range of from about 5 to 30 minutes is used. The shortest incubation time is limited by the variation in result that is produced by short incubations, and the longer incubation time is limited by the difficulty in measuring rapidly changing biology of the sperm cells with a long assay. Preferably, for current reagents, the assay incubation time is in the range from about 10 to about 30 minutes. More preferably, the assay should be run in the time frame of about 10 to about 20 minutes. Preferably, there is no lag time between the end of the incubation, washing and scoring sperm by cytometry, except that introduced by the required time to complete these steps. As a lag time increases, the sperm state may be adversely affected with respect to interpretation.

Sperm can be stabilized in the desired state by a variety of approaches. Stabilization is normally accomplished by adding a protective diluent (also called extender), such as the commercially manufactured BioXcell or diluent formulations such as TEST yolk buffer, or milk containing diluents. A number of compatible formulations are well known to those skilled in the art and are commercially available, and instructions for formulating others are available in the scientific literature. Preferably, BioXcell or an egg yolk containing one is used for a diluent, but this is not very important. Most important is the rapidity with which the temperature is lowered after diluent is added to sperm after the assay desired maturation point is determined.

Preferably, when the desired sperm state is reached, it is important to immediately add diluent preferably already cooled to 12° C. Immediately after diluent is added, the ejaculate preferably is transferred to a 4° C. cold room. Dilution in a plastic bag minimizes thermal mass of the container and is beneficial to rapid cooling. In the absence of rapid cooling, the sperm biological state may change. After cooling, doses of semen are normally dispensed into individual straws used to service cows. This process preferably is carried out at 4° C. as well. These straws can then be subjected to further cooling from 4° C. to the temperature of liquid nitrogen either immediately or after overnight incubation at 4° C. The procedures for dilution, stabilization, cooling and making straws are conventional procedures well known to those skilled in the art.

Improved fertility in artificial insemination has great commercial value for agriculture and in human clinical treatment. In agriculture, the profitability of the average dairy farm can more than double using the improvements provided by the present invention. There have been repeated attempts in the prior art to increase bull fertility that have generally failed or produced increases of 1% or less. In dairy farming, a 1% increase in fertility is worth $20 per cow per year while the average dairy farmer only earns approximately $75 per cow per year. A statistically significant increase in fertility of 7% produced using preferred embodiments of the present invention can more than double the profitability of the average dairy farm. The high value of fertility is because cows only produce milk around a pregnancy and a dry cow still must be fed, housed and attended to. The likelihood of a pregnancy decreases with each insemination and a non-producing cow must be culled from the herd. Because of this, all efforts are exhausted to increase fertility. Prior to the present invention, no one has increased fertility by identifying the changing state of the semen during the collection and processing procedures to identify and process in a state that produced higher fertility. Further, there is no meaningful loss of semen from process in accord with the present invention making it suitable for young sires with small collections that are increasingly used for high quality genetics and for high value bulls where semen is sold out for every dose available. Using the present invention, top genetic bull semen for herd improvement can be more affordable with greater certainty of conception.

Improved human male fertility also can be achievable with no additions to the sperm or medications for the patient. Research on both human and bovine ejaculates, using procedures in accord with the present invention, has shown identical patterns in the changes of the maturation state and ability to optimize the semen collection for fertility.

Healthcare costs for infertility treatments are substantial. It has been reported that 25% of couples seek treatment for infertility defined as the inability to achieve pregnancy after one year of unprotected sexual relations. Delayed household formation and societal changes have delayed child bearing which has a detrimental effect on success rates. Male fertility is the cause or is contributory in 40% of infertility and possibly in another 20% that go unexplained as to cause. Increased success rates in insemination could reduce the number of insemination procedures (average 3 cycles at a cost of about $1,500 per cycle) and reduce the need for more expensive IVF and ICSI procedures (1-3 cycles—costs range about $12,000-$20,000 per cycle). Processes in accord with the present invention also can improve the sperm selection for IVF and ICSI, improving those results and potentially reducing the number of procedures. Since Assisted Reproductive Technologies (ART) is not always paid by insurance, patients often delay or forgo expensive procedures for financial reasons decreasing the chances of success. Affordable, more successful insemination treatment could be the only solution for many patients. While the financial costs savings opportunities are substantial, the societal benefits are at least as significant. The stress of what is often years of treatment, medications and procedures takes its toll on individuals, relationships and marriages.

A diagnostic assay, using concepts of the present invention, can be used to evaluate doses of semen that were not processed in the manufacturing process control using the presently disclosed biomarker assay, and to predict the quality of their performance upon insemination. Although many tests have been applied as fertility predictors for performance of frozen straws upon insemination, none have proven successful. The presently disclosed assay procedure stands in sharp contrast to the traditional assays that involve DNA fragmentation, acrosomal status, calcium gradient measurement, and mitochondrial function, or multiple combinations of assays in attempt to obtain more accurate results. None of these traditional assays are directed against the key determinant of sperm potency: the presence in the semen dose of a cohort of sperm that are mature and ready to fertilize an egg. The most popular conclusion drawn from these traditional assay results is that fertility is difficult to predict in vitro. In accord with assays of the present invention, it is possible to predict fertility in vitro by applying presently disclosed techniques for detection of sperm maturation state to conventionally processed frozen and thawed semen doses. Tests have correctly discriminated 20 doses as either conventionally processed or processed by our assay.

The presently disclosed biomarker assay also can be used as a prelude to sperm separation enabling isolation of cells at the desired maturation state appropriate for the type of assisted reproductive technology intervention. Up to now, assisted reproductive technology has involved intervention at different reproductive stages. The simplest ART is intrauterine insemination (IUI). In contrast to natural intercourse, which deposits semen in the vagina, IUI deposits sperm in the uterus, moving all sperm past the cervix mechanically. In vitro fertilization mixes sperm with eggs. Intra-cytoplasmic egg injection involves placement of the sperm nucleus inside the egg via a needle. The maturation state of sperm during a natural intercourse is different at each stage corresponding to the different ARTs (see FIGS. 1, 24). In a vagina, the job of the sperm is to navigate through the cervical filter into the uterus. From the uterus, sperm must swim to the site of the egg and become capable of binding to the egg vestments prior to penetration of the egg plasma membrane. When the sperm is inside the egg, under natural conditions it no longer has an acrosome associated with it. The need for different maturation states of sperm for different reproductive interventions is only now becoming apparent. There are attempts to isolate sperm lacking the acrosome for use in intracytoplasmic sperm injection (ICSI) and attempts to isolate sperm with specific binding properties for use in IVF. Unfortunately, none of these approaches optimizes sperm at a specific maturation state. As a consequence, it has been reported that outcome in intracytoplasmic sperm injection is improved by acrosome removal (Gianaroli, 2010). Using the techniques of the present invention can prepare cells, and in addition, also enable a user to carry out isolation methods for selecting the desired cell population. Using the techniques of the present invention, a much larger number of sperm possessing the desired attributes can be obtained for use.

Those skilled in the art, upon consideration of the present disclosure including the drawings, may make additional procedures within the spirit and scope of the present invention.

LIST OF REFERENCES (WHICH ARE HEREBY INCORPORATED HEREIN BY REFERENCE)

Aitken R J and Baker M A (2008) The role of proteomics in understanding sperm cell biology. Int J Androl, 31, 295-302.
Bailey J L (2010) Factors regulating sperm capacitation. Syst Biol Reprod Med, 56, 334-348.
Bedford J M (1970) Sperm capacitation and fertilization in mammals. Biol Reprod, 2, Suppl-58.
Chang M. C. (1958) Capacitation of rabbit spermatozoa in the uterus with special references to the reproductive phases of the female. Endocrinology, 63, 619-628.
Cohen-Dayag A., Tur-Kaspa I., Dor J., Mashiach S., and Eisenbach M. (1995) Sperm capacitation in humans is transient and correlates with chemotactic responsiveness to follicular factors. Proc. Natl. Acad. Sci. U.S.A., 92, 11039-11043.
Correa, J. R., Zarmakoupis-Zavos, P. N. and Zavos, P. M. (1997) Quantitative and Qualitative Characteristics of Frozen-Thawed Bovine Spermatozoa Recovered Via a Conventional and a Standardized Swim-Up Technique. Tohuku J. Exp. Med., 181, 267-274.
Flesch, F., and Gadella, B. (2000) Dynamics of the mammalian sperm plasma membrane in the process of fertilization. Biochimica et Biophysica Acta, 1469: 197-235.
Foote R. H. and Kaprotht M. T. (2002) Large batch freezing of bull semen: effect of time of freezing and fructose on fertility. J. Dairy Sci, 85, 453-456.
Fraser, L. R. (2010) The "switching on" of mammalian spermatozoa: molecular events involved in promotion and regulation of capacitation. Molecular Reproduction and Development 77(3):197-208.
Gadella B. (2013) Dynamic regulation of sperm interactions with the zona pellucida prior to and after fertilization. Reproduction, Fertility and Development, 2013, 25, 26-37 http://dx.doi.org/10.1071/RD12277
Gianaroli, L., Magli, M. C., Ferraretti, A. P., Crippa, A., Lappi, M., Capitani, S., and Baccetti, B. (2010) Birefringence characteristics in sperm heads allow for the selection of reacted spermatozoa for intracytoplasmic sperm injection. Fertility and Sterility, 93(3): 807-813. doi: 10.1016/j.fertnstert.2008.10.024

Jenkins T. G. and Carrell D. T. (2011) The paternal epigenome and embryogenesis: poising mechanisms for development. Asian J. Androl., 13, 76-80.
Kim, K.-S., Foster, J. and Gerton, G. (2001) Differential Release of Guinea Pig Sperm Acrosomal Components During Exocytosis. Biology of Reproduction, 64: 148-156.
Mortimer D. (1991) Sperm preparation techniques and iatrogenic failures of in-vitro fertilization. Hum. Reprod., 6, 173-176.
Shojaei H., Kroetsch T., Wilde R., Blondin P., Kastelic J. P., and Thundathil J. C. (2012) Moribund sperm in frozen-thawed semen, and sperm motion end points post-thaw and post-swim-up, are related to fertility in Holstein A I bulls. Theriogenology, 77, 940-951.
Williams M., Hill C. J., Scudamore I., Dunphy B., Cooke I. D., and Barratt C. L. (1993) Sperm numbers and distribution within the human fallopian tube around ovulation. Hum. Reprod., 8, 2019-2026.

What is claimed:

1. A method for modifying the maturation state of mammalian sperm for use in an assisted reproductive technology (ART), said method comprising:
providing a mammalian ejaculate, and optionally freezing a portion of the ejaculate;
incubating an aliquot of the mammalian ejaculate under controlled temperature of from room temperature to about 40° C.;
assaying the aliquot of the mammalian ejaculate for a marker indicative of sperm cell maturation during an incubation period to determine sperm maturation state by observing the percent of cells in the aliquot that are positive for the marker indicative of sperm cell maturation, wherein the marker indicative of sperm cell maturation is a lectin;
repeating the assaying step with successive aliquots at intervals during incubation to determine in real-time an initial peak in the percentage of positive cells, a decline to a minima, a subsequent peak, and a subsequent decline in the percentage of positive cells, wherein multiple peaks are indicative of cycling sperm; and
processing remaining sperm from the mammalian ejaculate for assisted reproduction at a time after the percentage of positive cells in the latest aliquot being assayed declines to the first minima from the initial peak or to a second minima from the subsequent peak in the percentage of positive cells, wherein the method effectuates preparation of mature sperm.

2. The method of claim 1, wherein the providing step includes collecting the mammalian ejaculate from a mammal using a collection device prewarmed to about the body temperature of the mammal.

3. The method of claim 2, wherein the mammal is bovine and the collection device is prewarmed to a temperature in the range of about 30-40° C.

4. The method of claim 1, wherein the assaying step includes: mixing the aliquot with reagents capable of producing fluorescence in connection with a positive reaction with a sperm cell; and determining a percentage of fluorescent positive cells.

5. The method of claim 4, wherein the reagents include an antibody to the marker and the antibody is labeled with a fluorescent label.

6. The method of claim 4, wherein the reagents include a primary antibody, and a secondary antibody that is labeled with a fluorescent label.

7. The method of claim 4, wherein the reagents include a stabilizer for the sperm cells.

8. The method of claim 4, wherein the determination of percent positive cells is made by a method selected from the group consisting of antibody-based, dye-based, motility-based and microscopy based procedures.

9. The method of claim 1, wherein processing includes stabilizing the ejaculate remaining for further processing for ART.

10. The method of claim 9, wherein the further processing includes making straws having a predetermined amount of sperm cells and freezing the straws for artificial insemination.

11. The method of claim 1, wherein the marker is indicative of sperm cell capacitation.

12. The method of claim 1, wherein the lectin binds peanut agglutinin.

13. The method of claim 1, wherein the lectin binds *Pisum sativum* agglutinin.

14. The method of claim 1, wherein the processing step is performed within 30 minutes of the initial peak but prior to the subsequent peak.

\* \* \* \* \*